(12) United States Patent
Zemel et al.

(10) Patent No.: US 7,704,979 B2
(45) Date of Patent: *Apr. 27, 2010

(54) MATERIALS AND METHODS FOR THE TREATMENT OR PREVENTION OF OBESITY

(75) Inventors: Michael B. Zemel, Knoxville, TN (US); Hang Shi, Knoxville, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 597 days.

This patent is subject to a terminal disclaimer.

(21) Appl. No.: 10/017,568

(22) Filed: Dec. 14, 2001

(65) Prior Publication Data

US 2002/0192264 A1 Dec. 19, 2002

Related U.S. Application Data

(63) Continuation-in-part of application No. 09/654,357, filed on Sep. 1, 2000, now Pat. No. 6,384,087, and a continuation-in-part of application No. PCT/US01/27432, filed on Sep. 4, 2001.

(51) Int. Cl.
*A01N 45/00* (2006.01)
(52) U.S. Cl. .................. 514/167; 514/168; 514/909
(58) Field of Classification Search ............. 514/909, 514/143.1, 738–39, 844, 952, 167, 168, 729; 530/388.22; 424/401, 63
See application file for complete search history.

(56) References Cited

U.S. PATENT DOCUMENTS

| | | | |
|---|---|---|---|
| 3,621,024 A | 11/1971 | Nieper | |
| 4,027,043 A | 5/1977 | Schroeder et al. | |
| 4,237,118 A | 12/1980 | Howard | |
| 4,298,601 A | 11/1981 | Howard | |
| 4,784,871 A | 11/1988 | Park | |
| 4,833,128 A | 5/1989 | Solomon et al. | |
| 5,158,310 A | 10/1992 | Tannehill et al. | |

(Continued)

FOREIGN PATENT DOCUMENTS

BE 723952 4/1969

(Continued)

OTHER PUBLICATIONS

Larsson et al., Clinical Orthopaedics and Related Research, 1977, 127, 228-235.*

(Continued)

*Primary Examiner*—Johann R Richter
*Assistant Examiner*—Abigail Fisher
(74) *Attorney, Agent, or Firm*—Venable LLP; Michael A. Gollin; Thomas F. Berry

(57) ABSTRACT

The subject invention provides methods of inducing the loss of adipose tissue by providing a diet high in calcium. In one aspect of the invention, the calcium is provided in the form of dairy products. In yet another aspect of the invention, calcium is provided in the form of a dietary supplement, such as calcium carbonate, of vitamin supplements. Methods of suppressing $[Ca^{2+}]_i$ levels in individuals are also provided. The subject invention also provides methods of stimulating lipolysis, inhibiting lipogenesis, and increasing the expression of white adipose tissue uncoupling protein 2 (UPC2). The subject invention also provides methods of increasing the core temperature of an individual.

19 Claims, 12 Drawing Sheets

U.S. PATENT DOCUMENTS

| | | | |
|---|---|---|---|
| 5,484,623 | A | 1/1996 | McLean |
| 5,538,743 | A | 7/1996 | Heinemann et al. |
| 5,683,725 | A | 11/1997 | Malik et al. |
| 5,698,222 | A | 12/1997 | Mazer et al. |
| 5,739,106 | A | 4/1998 | Rink et al. |
| 5,855,949 | A | 1/1999 | McLean |
| 5,879,163 | A | 3/1999 | Brown et al. |
| 5,914,326 | A | 6/1999 | McCarty et al. |
| 6,013,622 | A | 1/2000 | Bruno et al. |
| 6,071,544 | A | 6/2000 | Sunvold |
| 6,136,349 | A | 10/2000 | Karppanen et al. |
| 6,159,530 | A | 12/2000 | Christiansen et al. |
| 6,299,914 | B1 | 10/2001 | Christiansen et al. |
| 6,384,088 | B1 | 5/2002 | Hinz |
| 6,403,657 | B1 | 6/2002 | Hinz |

FOREIGN PATENT DOCUMENTS

| | | |
|---|---|---|
| CN | 1086384 | 5/1994 |
| GB | 2 348 794 | 10/2000 |
| JP | 55-088685 | 7/1980 |
| JP | 63-196229 | 8/1988 |
| JP | 04-183360 | 6/1992 |
| JP | 07-147935 | 6/1995 |
| JP | 09-173019 | 7/1997 |
| JP | 10-066513 | 3/1998 |
| JP | 2000-189108 | 7/2000 |
| JP | 2001-161285 | 6/2001 |
| JP | 2001-509013 | 7/2001 |
| WO | WO 98/28989 | 7/1998 |
| WO | WO 99/03464 | 1/1999 |
| WO | WO 99/11254 | 3/1999 |

OTHER PUBLICATIONS

McCarthy, Remedy, Mar./Apr. 2000, 11.*
Jequier, Am. J. Clin. Nutr., 1987, 45, 1035-47.*
Merriam-Webster Dictionary,http://www.merriam-webster.com/dictionary/attenuating, obtained on Jan. 10, 2008, pp. 1-2.*
Peterson et al., Journal of Nutrition, 1992, 122, 137-144.*
Sanwa Kagaku Kenkyusho Co, "Stabilised Oligo Peptide Composition for Sleep-Improving Drug Containing Oligo-Peptide and Bovine Bone Powder as Calcium Salt, for Obesity Treatment, etc.," Database WPI, Section Ch, Week 199028, Derwent Publications Ltd., London, GB; 804, AN 1990-214417, XP002206900 & JP 02 145525 A, Jun. 5, 1990—abstract.
Meiji Seika Kaisha, "Food Compound for Overweight Clients—Obtained by Blending Water Soluble Dietary Fibers and Insoluble Calcium Compound in Acidic Conditions, e.g., Gastric Juice," Database WPI, Section Ch, Week 199211, Derwent Publications Ltd., London, GB; AN 1992-083488, XP002206898 & JP 04 023968 A, Jan. 28, 1992—abstract.
Meiji Seika Kaisha, "Diet or Diabetic Food—Contains Water-Soluble Food Fiber, Preferably Arginic Acid (Salt), and Insoluble Calcium Compound," Database WPI, Section Ch, Week 199532, Derwent Publications Ltd., London, GB; AN 1995-242723, XP002206899 & JP 07 147935 A, Jun. 13, 1995—abstract.
Garrow, J.S., et al., "Inpatient-Outpatient Randomized Comparison of Cambridge Diet Versus Milk Diet in 17 Obese Women Over 24 Weeks," *International Journal of Obesity*, 13: 521-529 (1989).
McCarron, David A., et al., "Blood Pressure and Nutrient Intake in the United States," *Science* 224:1392-1398 (1984).
Metz, J.A., et al., "Modification of Total Body Fat in Spontaneously Hypertensive Rats and Wistar-Kyoto Rats by Dietary Calcium and Sodium," *American Journal of Hypertension*, Inc. 1:58-60 (1988).
Skinner, J., et al., "Does Dietary Calcium Have a Role in Body Fat Mass Accumulation in Young Children?," *Nutrition*, suppl No. 34, pp. 45S (1999).
Summerbell, Carolyn D., et al., "Randomised Controlled Trial of Novel, Simple, and Well Supervised Weight Reducing Diets in Outpatients," *BMJ* 317:1487-1489 (1998).

Teegarden, D., et al., "Calcium Intake Relates to Change in Body Weight in Young Women," *The FASEB Journal* 13:A873, Abstracts Part II No. 660.4 (1999).
Zemel, Michael B., "Nutritional and Endocrine Modulation of Intracellular Calcium: Implications in Obesity, Insulin Resistance and Hypertension," *Molecular and Cellular Biochemistry* 188:129-136 (1998).
Xue, B., Greenberg, A.G., Kraemer, F.B. And Zemel, M.B., [2001] "Mechanism of Intracellular Calcium ($[Ca2+]1$) Inhibition of Lipolysis in Human Adipocytes," FASEB J. 15:2527-2529 [Nov. 2001](expanded version on-line: FASEB J 10.1096/fj.01-0278fje, Published on-line Sep. 17, 2001).
Shi, H., Norman, A.W., Okamura, W.H., Sen, A., Zemel, M.B., [2001]"$1\alpha,25$-dihyroxyvitamin D3 modulates human adipocyte metabolism via nongenomic action", FASEB J. 15:2751-2753 [Dec. 2001] (expanded version on-line: FASEB J 10.1096/fj.01-0584.fje. Published on-line Oct. 17, 2001).
Zemel, M.B., Geng, X, [Sep. 2001] "Dietary calcium and yogurt accelerate body fat loss secondary to caloric restriction in aP2-agouti transgenic mice," Obesity Res 9:146S.
Burrington, Kimberly J., "Food Product: Dairy Ingredients for Health," [Oct. 1999] <http://www.karlloren.com/Diabetest/diet/milk/p5.htm><Nov. 20, 2001 >, pp. 1 of 17.
Lin, Yi-Chin, et al., "Dairy Calcium is Related to Change in Body Composition During a Two-Year Exercise Intervention in Young Women", Journal of the American College of Nutrition, vol. 19, No. 6, 754-760 (2000), pp. 754-760.
Davies, K. Michael, "Calcium Intake and Body Weight", The Journal of Clinical Endocrinology & Metabolism, Vol. 85, No. 12, Dec. 2000, pp. 4635-4638.
Carruth, BR and Skinner, JD, "The Role of Dietary Calcium and Other Nutrients in Moderating Body Fat in Preschool Children", International Journal of Obesity, vol. 25, No. 4, Apr. 2001, pp. 559-566.
Zemel, Michael B., "Dietary Calcium and Dairy Products Accelerate Weight and Fat Loss During Energy Restriction in Obese Adults," American Journal of Clinical Nutrition, [2000] 75(suppl):a342s.
Heaney, Robert P., "Calcium Needs of the Elderly to Reduce Fracture Risk," Journal of the American College of Nutrition, vol. 20, No. 20, 192S-197S (2001).
Massey, Linda K., "Dairy Food Consumption, Blood Pressure and Stroke," American Society for Nutritional Sciences, 2001, pp. 1875-1878.
Bouillon, B., et al., "Structure-Function Relationships In The Vitamin D Endocrine System," Endocrine Rev. (1995) pp. 200-57, vol. 16.
Norman, A.W., "Receptor for $1\alpha,25(OH)_2$-$D_3$: Past, Present, and Future," J. Bone. Miner. Res. (1998) pp. 1360-69, vol. 13.
Norman, A., et al., "Demonstration That $1\beta,25$-Dihyroxyvitamin $D_3$ Is An Antagonist Of The Nongenomic But Genomic Biological Response And Biological Profile of the Three A-Ring Diastereomers Of $1\alpha,25$-Dihydroxyvitamin $D_3$", J. Biol. Chem. (1993) pp. 20022-30, vol. 268.
Hirsch, "Got Milk? Getting Thinner?", *Express*,Tuesday, Jul. 19, 2005, p. 10.
Herdick et al., "Carboxylic Ester Antagonists of $1\alpha,25$-dihydroxyvitamin $D_3$ Show Cell-Specific Actions" (Research Paper XP-001069553), *Chemistry & Biology 2000*, vol. 7 No. 11, pp. 885-894.
Laine Tabbita, "The Milk Mustache Campaign (agcommcase.ifas.ufl.edu/mustache.html) Report to Congress on the National Dairy Promotion and Research Program and the National Fluid Milk Processor Promotion Program," Jul. 1, 1998.
Jones Sports Mustache for Milk, Las Vegas Review Journal 1999 (Dialog: File 397:00150522).
U.S. Government questions effectiveness of Milk advertising, Dairy Farmer, 1999 (Dialog file 112:01171968.
Jenny Hope, Crash Diets do work single food regimes knock off the pounds faster than conventional calorie cutting, Daily Mail, 1998 Dialog file 781:04337869.
Denke, Margo A., et al. "Short-Term Dietary Calcium Fortification Increases Fecal Saturated Fat Content and Reduces Serum Lipids in Men", Journal of Nutrition vol. 123, No. 6, Jun. 1993, pp. 1047-1053. Copyright © 1993 by American Society for Nutrition.

Bingzhong Xue, et al., "The agouti gene product inhibits lipolysis in human adiopocyteds via a Ca2+—dependent mechanism", The FASEB Journal, vol. 12, pp. 1391-1396, Oct. 1998.

Catherine B. Chan, et al., "Overexpression of Uncouplin Protein 2 Inhibits Glucose-Stimulated Insulin Secretion From Rat Islets", Diabetes, vol. 48, pp. 1-5, Jul. 1999.

EJ Michaud, et al., "Obesity and the Adipocyte", Journal of Endocrinology, 1997, vol. 155, pp. 207-209, published in Great Britain.

Hang Shi, et al., "Role of Intracellular Calcium in Human Adiopocyte Differentiation", Physiol Genomics, vol. 3, pp. 75-82, 2000 (article published online before print).

J.H. Kim, et al., "Agouti Regulation of Intracellular Calcium : Role of Melancortin Receptors", The American Physiological Society, vol. 35, pp. E379-384, 1997.

Judith Cook, et al., "The Contribution Made, by School Milk to the Nutrition of Primary Schoolchildren", British Medical Journal, 1975, vol. 34, pp. 91-103, London.

Lewis Landsberg, M.D., "Weight Reduction and Obesity", Clin. And Exper. Hypertension 1999, vol. 21(5&6), pp. 763-768.

Michael B. Zemel, et al., "Agouti Regulation of Intracellular Calcium: Role in the Insulin Resistance of Viable Yellow Mice", Proc. Natl. Acad. Science, vol. 92, pp. 4733-4737, May 1995.

National Dairy Council, "Study Heralds the Pwer of Lowfat Dairy Foods in Helping Control Body Fat and Helping Reduce the Risk of Obesity", press release, Nov. 17, 1999.

Robert C. Klesges, PhD, et al., "Predictors of Milk Consumption in a Population of 17-to-35-Year-Ol Military Personnel", Journal of the American Dietetic Association, Jul. 1999, vol. 99, No. 7, pp. 821-838, publisher—Debra McBride.

Scott Ackley, et al., "Dairy Products, Calcium, and Blood Pressure", The American Journal of Clinical Nutrition, vol. 38, pp. 457-461, Sep. 1983.

www.sciencedaily.com, "Calcium May Curb Weight Gain in Young Women", website, Apr. 1999, (adapted from a news release issued by Purdue University).

Y. Hata, M Yamamoto, M. Ohni, K. Nakajima, Y. Nakamura and T. Takano, "A Placebo-Controlled Study of the Effect of Sour Milk on Blood Pressure in Hypertensive Subjects", Am J Clin Nutr, 1996;64,pp. 767-771.

Yi-Chin Lin, MS, PhD, et al., "Dairy Calcium is Related to Changes in Body Composition During a Two-year Exercise Intervention in Young Women", Journal of the American College of Nutrition, 2000, vol. 19, No. 6, pp. 754-760, published by the American College of Nutrition.

Milk in Wikipedia (http://en.wikipedia.org/wiki/Whole_Milk).

Dietary Supplement Fact Sheet: Calcium (http://dietary-supplements.info.nih.gov/factsheets/calcium.asp).

Ask a Scientist (http://www.newton.dep.anl.gov/askasci/chem99/chem99135.htm).

Office Action of Oct. 8, 2008, issued in U.S. Appl. No. 10/827,353.
Office Action of Sep. 19, 2008, issued in U.S. Appl. No. 10/827,301.
Office Action of Aug. 8, 2008, issued in U.S. Appl. No. 10/827,297.
Office Action of Sep. 24, 2008, issued in U.S. Appl. No. 10/827,296.
Goodman and Gilman's, the Pharmacological Basis of Therapeutics.
Merck Manual Home Edition online article entitled, "Introduction: Coronary Artery Disease"—accessed Sep. 19, 2008 at www.merck.com/mmhe/print/sec03/ch033/cho33a.html.

Taggu et al. "Treating Cardiovascular disease in women," Menopause International, 2007, 13, pp. 159-164.

Eckel, R.H. Obesity and Heart Disease, Circulation, 1997, vol. 96, pp. 3248-2350.

Office Action of May 28, 2008, issued in U.S. Appl. No. 10/827,307.
Final Office Action of Sep. 5, 2008, issued in U.S. Appl. No. 10/827,309.
Office Action of Jul. 8, 2008, issued in U.S. Appl. No. 10/066,057.
Bronner et al., "Recent Advances in Nutritional Science", Journal of Nutrition, 1999, 129, pp. 9-12.
Office Action of Jan. 15. 2009, issued in U.S. Appl. No. 10/066,057.
Börjeson, M. [1976] "The Aetiology of Obesity in Children," Acta Pædiatr Scan 65:279-87.

Carper, Jean [2000] "Amazing Food Facts that Astound the Experts," USA Weekend, Aug. 18-20, 2000, p. 4.

CNN, Zemel Weight Loss Story, Mar. 30, 2000; And National Dairy Council, "Dairy Foods May Help Control Weight Gain," Jun. 9, 2000, videotape.

Colino, S., "Advanced Calcium, Lose Weight, avoid PMS and ward off cancer, all with one basic nutritional element," Women's Sports & Fitness, Mar. 2000, p. 56.

Davis, J.; "Weight-Loss Tip: Add Extra Calcium to a Low-Fat Diet, Low-Fat Dairy Products May Help Weight Loss, Control," WebMDHealth, Apr. 17, 2000 (printed from website), Publisher: 2000 Healtheon/WebMD.

Fleet, J.C. [1999] "Vitamin D. Receptors: Not Just in the Nucleus Anymore," Nutrition Reviews vol. 57, No. 2, pp. 60-2.

Fleury, Christophe, et al. [1997] "Uncoupling Protein-2: a Novel Gene Linked to Obesity and Hyperinsulinemia", Nature Genetics 15:269-72.

Gimeno, R. et al. [1997] "Cloning and Characterization of an Uncoupling Protein Homolog: a Potential Molecular Mediatoï of Human Thermogenesis," Diabetes 46:900-06.

Jones, Brynn H., et al. [1997] "Angiotensin II Increases Lipogenesis in 3T3-L1 and Human Adipose Cells," Endocrinology, vol. 138, No. 4, pp. 1512-19.

Kim, Jung Han, et al. [1996] "The Effects of Calcium Channel Blockade on Agouti-Induced Obesity", The FASEB Journal 10:1646-52.

Lange, D., "The Calcium Diet", Allure, Aug. 2000, p. 84.

Maslowska, M. et al. [1998] "Site Specific Binding of Acylation Stimulating Protein (ASP) in Human Adipose Tissue," Int. J. Obesity 22:S108 (P50).

McCarthy, L., "Got Milk, Lose Weight?", Remedy Magazine, Mar./Apr. 2000, p. 11.

Moll, P.P., et al. [1991] "The Genetic and Environmental Sources of Body Mass Index Variability: The Muscatine Ponderosity Family Study," Am. J. Hum. Genet. 49:1243-55.

Mundell, E.J., "Trying to Lose Weight? Calcium May Help", Reuters health report, Apr. 17, 2000, (printed from website), Publisher: Reuters Limited.

Mynatt, R. L., et al. [1997] "Combined Effects of Insulin Treatment and Adipose Tissue-Specific Agouti Expression on the Development of Obesity," Proc. Natl. Acad. Sci. USA 94:919-922.

Nemere, I., et al. [1998] "Identification of a Membrane Receptor for 1,25-Dihydroxyvitamin $D_3$ Which Mediates Rapid Activation of Protein Kinase C," J. Of Bone and Mineral Research 13:1353-59.

Pantalone, M., "Hello Calcium, Goodbye Fat," UT Agriculture, Fall 2000, pp. 5-7.

Rabkin, R., "Calcium Promotes Weight Loss," Family Circle, Oct. 3, 2000, p. 98.

Raloff, J.; "Calcium May Become a Dieter's Best Friend", Science News, Apr. 29, 2000, p. 277, vol. 157.

Shi, Hang, et al. [1999] "Role of the Sulfonylurea Receptor in Regulating Human Adipocyte Metabolism," The FASEB Journal 13:1833-38.

Shi, H. et al. [2000] "Effects of Dietary Calcium on Adipocyte Lipid Metabolism and Body Weight Regulation in Energy-Restricted Mice," FASEB J 14:555.3 (p. A790).

Shi, H. et al. [2000] "1, 25-Dihydroxyvitamin D $(1,25-(OH)_2-D)$ Inhibits Uncoupling Protein 2 (UCP2) Expression in Human Adipocytes," Obesity Research 8(1):52S (O154).

Shi, H. at al. [2001] "Effects of Dietary Calcium on Adipocyte Lipid Metabolism and Body Weight Regulation in Energy-Restricted aP2-agouti Transgenic Mice," FASEB J 15:291-3 and 10.1096/fj.00-0584fje.

Shi, H. et al. [2001] "1α, 25-Dihydroxyvitamin $D_3$ Modulates Human Adipocyte Metabolism via Nongenomic Action," FASEB J 15:835.6 (p. A1091).

Smith, S, "Functional Foods . . . Potential New Functional Qualities of Dairy Foods", NCC Newsletter, 2001, pp. 34-5, vol. 3, issue 2; Publisher: Nutrition in Complementary Care.

Sobel, R.K. [2000] "Catching' the Fat Bug," U.S. News & World Report p. 64.

Summerbell, C.D., et al. [1998] "Randomised Controlled Trial of Novel, Simple, and Well Supervised Weight Reducing Diets in Outpatients," *BMJ* 317:1487-89.

Unknown, "5-Step Fat-Blasting Diet," *Prevention Magazine*, Jun. 2000, p. 151.

Unknown, "Calcium and Weight-Loss", *Medizine*, Jan.-Feb.-Mar. 2001, p. 52.

Zemel, M. et al [1999] "Synergistism between Diet-Induced Hyperinsulinemia and Adipocyte-Specific Agouti Expression," *FASEB J* 13:660.3 (p. A873).

Zemel, M. at at [1999] "Calcium and Calcium-Rich Dairy Products Reduce Body Fat," *FASEB J* 12:LB211.

Zemel, M., "Readers Want to Know", *Bottom Line/Health*, Oct. 2000.

Zemel, M.B., et al. [2000] "Regulation of Adiposity by Dietary Calcium," *The FASEB Journal* vol. 14, No. 9, pp. 1132-7.

Zemel, M. et al [2001] "Effects of Calcium-Fortified Breakfast Cereal on Adiposity in a Transgenic Mouse Model of Obesity," *FASEB J* 15:480.7 (p. A598).

Zemel, P. et al. [2000] "Increasing Dietary Calcium and Dairy Product Consumption Reduces the Relative Risk of Obesity in Humans," *Obesity Research* 8(1):118 (HT-04).

Porthouse et al.; Randomised controlled trial of calcium and supplementation with cholecalciferol (vitamin D 3) for prevention of fractures in primary care; BMJ; vol. 330, Apr. 30, 2005; pp. 1-6.

Heymsfield et al., Weight management using a meal replacement strategy: meta and pooling analysis from six studies; International Journal of Obesity (2003), vol. 27, pp. 537-549.

Martinez et al.; Calcium, Vitamin D, and Colorectal Cancer: a Review of the Epidemiologic Evidence; Cancer Epidemiology, Biomarkers & Prevention; vol. 7, Feb. 1998; pp. 163-168.

Pfeifer et al.; Effects of a Short-Term Vitamin D and Calcium Supplementation on Body Sway and Secondary Hyperparathyroidism in Elderly Women; Journal of Bone and Mineral Research; vol. 15, No. 6; 2000; pp. 1113-1118.

Pittas et al.; The Role of Vitamin D and Calcium in Type 2 Diabetes. A Systematic Review and Meta-Analysis; The Journal of Clinical Endocrinology & Metabolism 92(6); 2007; pp. 2017-2029.

Zemel, MB, Calcium Modulation of Hypertension and Obesity: Mechanisms and Implications. Journal of the American College of Nutrition, vol. 20, No. 5, 428S-435S (2001).

* cited by examiner

FIG. 10A

MATERIALS AND METHODS FOR THE TREATMENT OR PREVENTION OF OBESITY

CROSS-REFERENCE TO RELATED APPLICATION(S)

The present application is a continuation-in-part of U.S. application Ser. No. 09/654,357, filed Sep. 1, 2000, now U.S. Pat. No. 6,384,087, and International Patent Application No. PCT/US01/27432, filed Sep. 4, 2001, both of which are hereby incorporated by reference herein in their entireties, including any figures, tables, nucleic acid sequences, amino acid sequences, or drawings.

BACKGROUND OF THE INVENTION

The regulation of body weight, and particularly body fat, in animals is a complex process having enormous implications for the health and well being of humans and other animals. Excess body weight and/or an excess of body fat relative to lean body mass has been associated with a wide range of health problems including coronary artery diseases, stroke, and diabetes.

It has been estimated that half of all Americans are overweight. Within the United States about 24% of men and 27% of women defined as mildly to severely obese. Individuals 20% over ideal weight guidelines are considered obese. Obesity is classified as mild (20-40% overweight), moderate (41-100% overweight), and severe (>100%) overweight. Severe obesity is relatively rare, affecting less than 0.5% of all obese individuals and about 0.1% of the total population.

Obesity is not just a problem for humans. Many animals also suffer adverse consequences related to obesity. For example, approximately 10 to 40% of cats receiving veterinary care have been reported to be overweight. Factors contributing to feline obesity include a sedentary lifestyle, confinement to indoors, and neutering. Obese cats have a greater risk for certain diseases including osteoarthritis, ligament injuries, perineal dermatitis, diabetes mellitus, cardiomyopathy, and urologic syndrome. Therefore, it is critical to maintain a healthy weight in order to minimize disease risk. (See, U.S. Pat. No. 6,071,544.)

Obesity in humans is treated by a variety of means ranging from surgical procedures (gastric bypass) for the severely obese to diet therapy, behavior modification, and medication for the mildly to moderately obese. Management of moderate and mild obesity is typically performed by the individual and commercial organizations which provide behavior modification programs and, in some cases, prepackaged diets. The medical community recommends that diet treatments be administered under medical supervision.

The range of treatments for obesity reflects the complexity of the processes involved in weight regulation and the current lack of understanding of these processes. Recent reports have even implicated viruses as a possible causative factor in obesity (U.S. News and World Report, Aug. 7, 2000). There are also numerous reports of possible genetic bases for a predisposition to obesity. Moll et al. have reported that, in many populations, obesity seems to be controlled by a few genetic loci (Moll, et al., *Am. J. Hum. Gen.* 49:1243 (1991)). In addition, human twin studies strongly suggest a substantial genetic basis in the control of body weight, with estimates of heritability of 80-90% (Simopoulos, A. P. and Childs, B., eds., 1989, in "Genetic Variation and Nutrition in Obesity," World Review of Nutrition and Diabetes, 63, S. Karger, Basel, Switzerland; Bojeson, M., *Acta. Paediatr. Scand.* (1976) 65:279-287).

Recombinant agouti protein, an obesity gene product, stimulates $Ca^{2+}$ influx in a variety of cells. Agouti also stimulates the expression and activity of fatty acid synthase (FAS), a key enzyme in de novo lipogenesis, and inhibits basal and agonist-stimulated lipolysis in human and murine adipocytes via a $Ca^{2+}$-dependent mechanism. These effects can be mimicked in the absence of agouti by either receptor or voltage-mediated $Ca^{2+}$ channel activation and inhibited by a $Ca^{2+}$ channel antagonist, such as nifedipine.

Recent data demonstrated that 1, 25-dihydroxyvitamin D $(1,25-(OH)_2-D)$ causes a significant and sustained increase in intracellular calcium concentrations $([Ca^{2+}]_i)$ in primary cultured human adipocytes and a corresponding inhibition of lipolysis (Zemel, et al., *FASEB J.* (2000) 14:1132-1138). Increasing dietary calcium suppresses $[Ca^{2+}]_i$, inhibits 1,25-$(OH)_2-D$, and subsequently suppresses adiposity by stimulation of lipolysis and inhibition of lipogenesis. Consistent with these findings, increasing dietary calcium from 400 to 1000 mg/day resulted in a 4.9 kg reduction of body fat in humans over the course of one year (Zemel, et al., *FASEB J.* (2000) 14:1132-1138). Dietary calcium can also attenuate the diet-induced development of adiposity and promote weight loss in established obesity (Shi, H., et al., *FASEB J.* (2000) 555.3 (abstract)).

BRIEF SUMMARY OF THE INVENTION

The subject invention provides materials and methods for treating or avoiding obesity in humans and other animals. Advantageously, the materials and methods of the subject invention can be used to easily and efficiently achieve weight loss and/or prevent weight gain. In a preferred embodiment, the obesity-control benefits of the subject invention are achieved by providing a diet high in calcium. In one aspect of the invention, individuals are maintained on a restricted caloric diet.

In a specific embodiment of the subject invention, calcium is provided in the form of dairy products. In yet another aspect of the invention, calcium is provided in the form of a dietary supplement, such as calcium carbonate, or vitamin supplements.

The subject invention also provides methods of stimulating lipolysis, inhibiting lipogenesis, and increasing the expression of white adipose tissue uncoupling protein 2 (UCP2). The subject invention also provides methods of increasing the core temperature of an individual as well as methods of diagnosing, treating, and/or monitoring obesity. Methods of suppressing $[Ca^{2+}]_i$ levels in individuals are also provided.

The instant invention also provides methods of attenuating weight gain and adiposity in children and controlling weight gain in children by increasing the amounts of dietary calcium consumed by the children.

BRIEF DESCRIPTION OF THE DRAWINGS

FIGS. 10A-B show the effects of 6-week administration of high calcium diets on abdominal adipose tissue uncoupling protein 2 (UCP2) expression in energy-restricted (70% of ad lib) a P2-agouti transgenic mice. Upper panel (FIG. 10A): a representative northern blot from 8 replicates; lower panel (FIG. 10B): quantitative analysis of UCP2/actin mRNA density units. Data are expressed as mean±SE (n=8). *p<0.05 vs. basal diet.

DETAILED DISCLOSURE OF THE INVENTION

Figure 1:
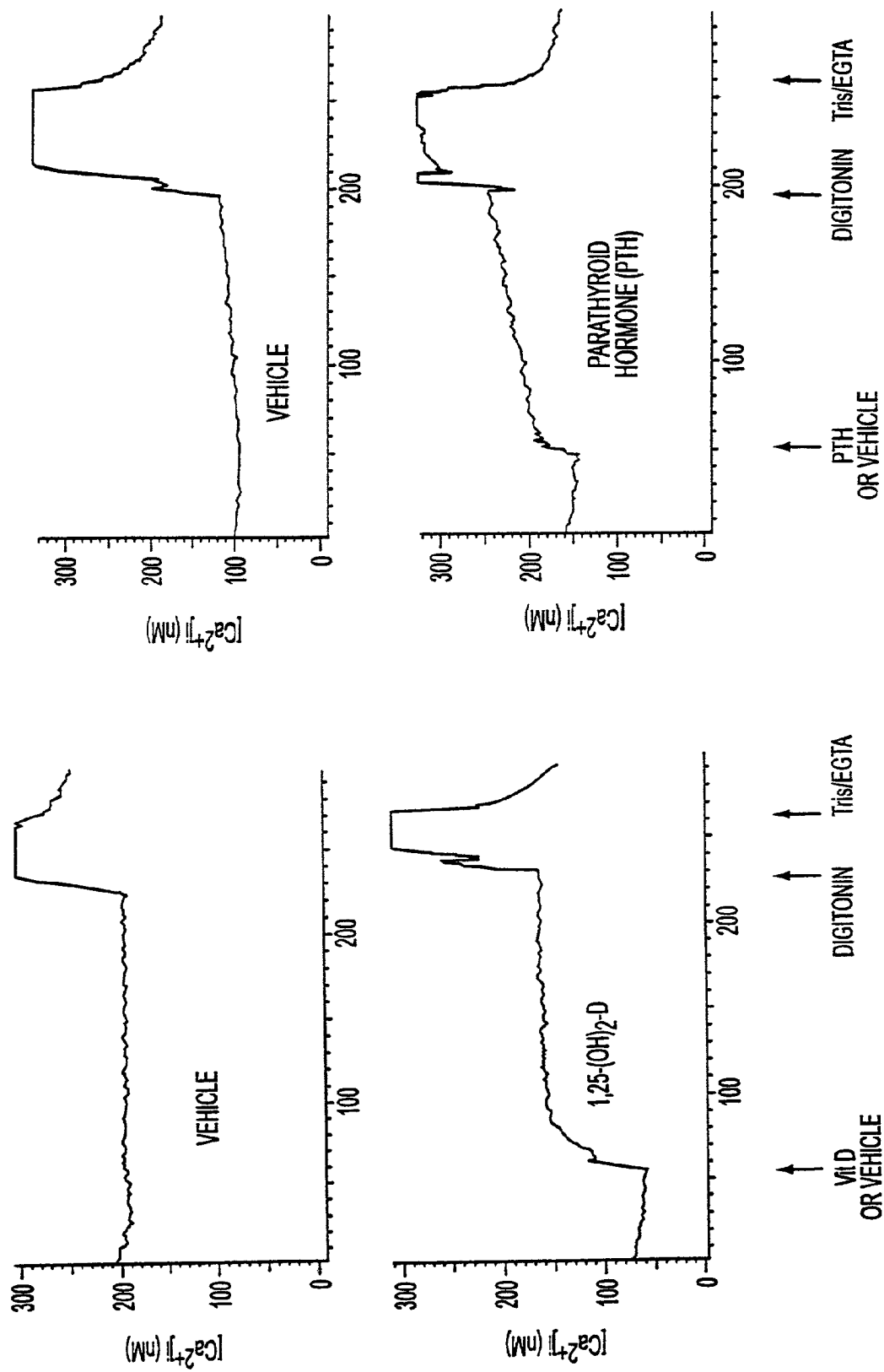
FIGS. 1A-B show the effects of $1,25-(OH)_2-D$ (left panel) and parathyroid hormone (right panel) on intracellular calcium in human adipocytes.

The subject invention provides materials and methods for treating or avoiding obesity in humans and other animals. Advantageously, the materials and methods of the subject invention can be used to easily and efficiently achieve weight loss and/or prevent weight gain. In a preferred embodiment, the body weight benefits of the subject invention are achieved by providing a diet high in calcium.

In a preferred embodiment, the subject invention provides methods of inducing the loss of adipose tissue in a human or other animal by increasing the ingestion of calcium. In one aspect of the invention, the calcium is provided in the form of a dairy product, such as milk, yogurt, or cheese. In another aspect of the invention, calcium is provided in the form of a dietary supplement, such as calcium carbonate or vitamin supplements. In yet another aspect of the invention, individuals are maintained on a restricted caloric diet.

Also provided are methods of decreasing intracellular calcium concentrations ($[Ca^{2+}]_i$), stimulating lipolysis, inhibiting lipogenesis, and increasing the expression of white adipose tissue uncoupling protein 2 (UCP2). The subject invention also provides methods of increasing the core temperature of an individual (thermogenesis). Each of these methods is practiced by increasing the amount of calcium ingested by an individual and, optionally, restricting the caloric intake of the individual.

Also provided are novel and advantageous methods of restoring normal body fat ratios in women post partum. In one such embodiment, the methods are practiced by identifying an individual who has recently given birth to a child and increasing the amount of dietary calcium consumed by the individual.

Methods of preventing or reducing the regain of weight lost after an initial period of dieting are also provided by the instant invention. This method can be practiced by identifying an individual who has lost weight as a result of a previous diet and increasing the amount of dietary calcium consumed by the individual.

Also provided are methods of decreasing the levels of calcitrophic hormones (1,25-(OH)$_2$-D) in an individual by increasing the amount of dietary calcium consumed by the individual.

The subject invention also provides methods of reducing the risk of obesity in a child by increasing the amount of calcium consumed by the child. Calcium intake can be accomplished by, for example, increasing the intake by the child of dairy products or other products containing high levels of calcium.

Also provided are methods of reducing, attenuating, or treating obesity comprising decreasing the levels of calcitrophic hormones (1,25-(OH)$_2$-D) in an individual by administration of a therapeutically effective amount of a 1,25-(OH)$_2$-D antagonist, for example dietary calcium. Other 1,25-(OH)$_2$-D antagonists include 1,25-(OH)$_2$-D neutralizing antibodies; soluble 1,25-(OH)$_2$-D receptor; fusion proteins comprising the 1,25-(OH)$_2$-D receptor (for example soluble forms of the 1,25-(OH)$_2$-D receptor fused to Ig heavy chains or moieties which preferentially target adipocytes); chemical compounds; and compounds containing calcium, such as calcium carbonate.

The subject invention also provides methods of reducing, treating, or attenuating obesity in an individual comprising the administration of therapeutically effective amounts of 1,25-(OH)$_2$-D receptor antagonists. Examples of such antagonists include antibodies which block the ligand binding site of the receptor; chemical compound antagonists of the receptor; and analogs, homologs, or isomers of 1,25-(OH)$_2$ -D which specifically bind to the 1,25-(OH)$_2$-D receptor but which antagonize the function of the receptor, for example 1β,25-dihydroxyvitamin D.

Calcium provided to an individual in accordance with the subject invention may take the form of, for example, a dairy product (for example milk, non-fat dry milk, yogurt, cheese, cottage cheese, ice cream or frozen yogurt), a nutrient supplement (such as calcium fortified vitamins and liquids supplemented with calcium), foodstuffs supplemented with calcium, or other foods high in calcium (for example, salmon, beans, tofu, spinach, turnip greens, kale, broccoli, waffles, pancakes, or pizza).

In a preferred embodiment, a therapeutically effective amount of dietary calcium is provided to an individual. A therapeutically effective amount of dietary calcium is an amount of calcium sufficient to induce weight loss, prevent weight gain, and/or increase the metabolic consumption of adipose tissue in a mammal.

Fusion proteins comprising the 1,25-$(OH)_2$-D receptor may be made according to methods known in the art. An exemplary type of fusion protein comprises the soluble form of the 1,25-$(OH)_2$-D receptor fused to Ig heavy chains according to the teachings of Capon et al. (U.S. Pat. Nos. 5,565,3375 and 5,336,603, hereby incorporated by reference in their entireties). In other embodiments, at least one 1,25-$(OH)_2$-D receptor (Nemere, et al, *J. Bone Miner. Res.* (1998) 13:1353-59; Fleet, et al., *Nutr. Rev.* (1999) 57:60-64) is incorporated into liposomes which are preferentially targeted to adipocytes using, for example, acylation stimulating protein (ASP) (Kalant et al., *Clin. Invest. Med.* (1995) 18 (Supp. B:B 10); Maslowska, et al, *Int. J. Obesity* (1998) 22:S108; Maslowska, et al., Acylation Stimulating Protein (ASP): Role in Adipose Tissue, in Progress in Obesity Research: 8, (1999), Ed. B. Gut-Grand and G. Ailhaud, John Libbey & Co.). In other embodiments, soluble forms of the 1,25-$(OH)_2$-D receptor may be coupled to adipocyte targeting agents such as the ASP. Soluble forms of the 1,25-$(OH)_2$-D receptor may be produced from the membrane bound form of the Vitamin D receptor according to methods known in the art. Coupling of one or more soluble 1,25-$(OH)_2$-D receptors to one or more adipocyte targeting agents may be accomplished recombinantly or using chemical crosslinking compounds, such as those sold by Pierce (Rockford, Ill.).

The term "individual" includes animals of avian, mammalian, or reptilian origin. Mammalian species which benefit from the disclosed methods include, and are not limited to, apes, chimpanzees, orangutans, humans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, and elephant seals. Reptiles include, and are not limited to, alligators, crocodiles, turtles, tortoises, snakes, iguanas, and/or other lizards. Avian species include, and are not limited to, chickens, turkeys, pigeons, quail, parrots, macaws, dove, Guinea hens, lovebirds, parakeets, flamingos, eagles, hawks, falcons, condor, ostriches, peacocks, ducks, and swans.

Each of the methods discussed above may further comprise restricting the caloric intake of an individual. Additionally, dietary products containing high levels of calcium may be provided to the individual in conjunction with a dietary plan. The dietary products may be provided to the individual on a regular or scheduled basis or on demand by the individual.

The methods of the subject invention may further comprise analysis of an individual's dietary intake. This analysis may be accomplished by analysis of the foods consumed by the individual as recorded on questionnaires regarding dietary intake or dietary logs completed by the individual. The logs or questionnaires may be in electronic or paper form.

Dietary intake information may be obtained by asking an individual questions in person or over the internet. In this aspect of the invention, questions can be posed to the individual regarding dietary habits and/or food consumption. The questions may be transmitted over the internet. Alternatively, forms or dietary logs can be transmitted to the customer over the internet. In either aspect of the invention, the information recorded by the individual can be returned to the web site by way of the internet. Dietary intake may be analyzed by a computer receiving the information from the individual through the internet.

The analysis of the individual's dietary intake may be performed by a computer after input of the data related to food consumption by the individual. The foods consumed by the individual, as well as the amounts, are compared to a database containing the nutritive values of the foods and the nutritional composition of the diet of the individual is provided. After analysis of the nutritional composition of the foods ingested by the individual, the amount of calcium consumed by the individual is provided. Recommendations regarding increases in the amount of calcium consumed by the individual, as well as sources of dietary calcium, may be provided from a database which compares the amount of calcium consumed with that found to optimize or induce weight loss.

In some instances, the caloric intake of an individual may be unmodified and caloric intake maybe ad lib. In other instances, it maybe desirable to reduce the caloric intake of the individual as part of the dietary plan. In one embodiment, the range of caloric intake of the individual is based upon gender. Caloric intake can range from about 200 to about 2500 kcal per day. In a preferred embodiment, the range of caloric intake is about 300-2400 kcal per day, preferably 500-2200 kcal per day, more preferably 700-2000 kcal per day, even more preferably 900-1700 kcal per day, and most preferably 1100-1500 kcal per day.

The weight/height ratio may be calculated by obtaining the weight of an individual in kilograms (kg) and dividing this value by the height of the individual in meters. Alternatively, the weight/height ratio of an individual may be obtained by multiplying the weight of the individual in pounds (lbs) by 703 and dividing this value by the square of the height of the individual (in inches (in)). These ratios are typically referred to as BMI. Thus, BMI=$kg/m^2$ or BMI=$(lbs.\times 703)/(in)^2$.

Where BMI is utilized as a measure of obesity, an individual is considered overweight when BMI values range between 25.0 and 29.9. Obesity is defined as BMI values greater than or equal to 30.0. The World Health Organization assigns BMI values as follows: 25.0-29.9, Grade I obesity (moderately overweight); 30-39.9, Grade II obesity (severely overweight); and 40.0 or greater, Grade III obesity (massive/ morbid obesity). Using weight tables, obesity is classified as mild (20-40% overweight), moderate (41-100% overweight), and severe (>100%) overweight. Individuals 20% over ideal weight guidelines are considered obese. Individuals 1-19.9% over ideal weight are classified as overweight.

Information related to the benefits of maintaining a normal weight, or optionally a normal weight/height ratio, dietary plan(s) containing high levels of calcium and printed matter disclosing the benefits of a high calcium diet may, optionally be provided in electronic or printed form and may be stored in a database.

A further aspect of the subject invention provides methods for promoting good health by providing a product with calcium wherein the provision of the product is accompanied by information regarding the benefits of the consumption of calcium with respect to the control of obesity. The calcium-containing product which is provided may be a dietary product such as, for example, cereals, milk and other dairy products, vegetables and other foodstuffs which are either naturally high in calcium or which are fortified with calcium. The product with calcium may also be a dietary supplement in the form of, for example, a pill or liquid.

The information regarding the benefits of the consumption of calcium with respect to the control of obesity would typically include, for example, a written or verbal explanation that the consumption of calcium is associated with weight loss and/or the prevention of weight gain. This information can be presented in such a fashion so that a potential purchaser and/or user of a product which contains calcium would understand that the consumption of the product with calcium could cause weight loss or reduce weight gain, and that the weight loss or reduction in weight gain from the use of the product would be directly attributable, at least in part, to the calcium present in the product.

In accordance with the subject invention, the information regarding the obesity-control benefits of a calcium-containing product may directly accompany the product. Thus, the information may be, for example, printed on a cereal box, a milk container, a cheese package, or an ice cream carton. The information may also be distributed through broader channels of communication including, for example, newspapers, magazines, direct mailings, radio, television, the internet, and billboards. Other distribution channels include verbal communication, pamphlet distribution, print media, audio tapes, magnetic media, digital media, audiovisual media, advertising, electronic mail, braille, electronic media, banner ads (including Internet banner ads and aircraft towed banners), fiber optics, and laser light shows. In a preferred embodiment, the information thus distributed regarding the benefits of calcium with regard to weight loss would identify a particular product with calcium which could be ingested in order to receive the obesity control benefits of calcium. The particular product could be identified by, for example, a trade name.

In a preferred embodiment, the obesity-control benefits of calcium are communicated by the provider of a particular calcium-containing product. The provider may be, for example, the owner of the trade name for the product. The information regarding the obesity-control benefits of calcium may also describe the benefits of a general class of products which contain calcium. Thus, the information may describe, for example, the obesity-control benefits of diary products which contain calcium. This information could be distributed by, for example, a trade association. Similarly, the information may describe the obesity-control benefits of dietary supplements which contain calcium.

The obesity-control information provided according to the subject invention maybe provided with, or without, information relating to other health benefits which may be attributed to calcium or which may be attributed to other components of the product which contains calcium. Thus, the obesity-control information may be accompanied by information concerning the benefits of calcium with respect to osteoporosis.

In a specific embodiment, information regarding calcium's obesity-control benefits would be practiced by a commercial entity having a financial interest in the sale of a product, or a class of products, which contain calcium. This would not typically be, for example, a doctor providing a specific patient with medical advice regarding a diet high in calcium without reference to particular trade names of products. This would also not typically include scientific articles describing research evaluating the obesity-control benefits of calcium.

The subject invention also provides articles of manufacture useful in stimulating the metabolic consumption of adipose tissue. Such articles of manufacture would typically comprise foodstuffs and printed materials disclosing the obesity-control advantages of high calcium diets. In one aspect of the invention, the printed materials may be in the form of pamphlets, package inserts, or as part of the package. In another aspect of the invention, the information may be embossed or imprinted on the foodstuff. Information so provided may include the amounts of calcium contained within the foodstuff, recommended levels of calcium intake necessary for the metabolically-assisted loss of adipose tissue, recommended BMI values, or recommended heights and weights for individuals. The foodstuff may be a solid or liquid. In one aspect of the invention, liquids with increased levels of calcium are provided as a dietary supplement for the treatment of obesity or stimulation of the metabolic consumption of adipose tissue. In this aspect of the invention, the liquids may be color coded to indicate the amounts of calcium contained therein. By way of example, food coloring additives are introduced into the liquid to indicate the amounts of calcium contained therein. A green colored liquid may contain 100 mg of calcium per serving, a yellow liquid may contain 200 mg of calcium per serving, and a magenta liquid may contain 500 mg of calcium per serving.

Example 1

Regulation of Adiposity by Dietary Calcium

Materials and Methods

Isolation and Culture of Human Adipocytes

Human subcutaneous adipose tissue was obtained from patients with no known history of metabolic disorders undergoing abdominal plastic surgery. Adipocytes were isolated by washing, mincing, collagenase digestion, and filtration as described previously and cultured in Dulbecco's modified Eagle's medium supplemented with 1% fetal bovine serum, penicillin (100 IU/ml), streptomycin (100 µg/ml), and gentamicin (50 µg/ml). Cells were cultured in suspension and maintained in a thin layer at the top of the culture media, which was changed every day. Cells were studied about 72 hours after isolation and were serum-starved prior to study.

Animal and Diets

To evaluate the role of dietary calcium in regulating adiposity in vivo, transgenic mice expressing agouti specifically in adipocytes under the control of the aP2 promoter were studied. These animals exhibit a normal pattern of leptin expression and activity similar to that found in humans and exhibit a human pattern (adipocyte-specific) of agouti expression. These mice are useful models for diet-induced obesity in that they are not obese on a standard AIN-93G diet, but become obese in response to hyperinsulinemia induced by either insulin administration or high sucrose diets. Male aP2-agouti transgenic animals from our colony were placed at 6 wk of age on a modified AIN 93-G diet with suboptimal calcium (0.4%), sucrose as the sole carbohydrate source, and fat increased to 25% of energy with lard. They were randomized to four groups, as follows. The basal group continued this diet with no modifications; a high calcium group received the basal diet supplemented with $CaCO_3$ to increase dietary calcium by three-fold to 1.2%; a medium dairy diet, in which 25% of the protein was replaced by non-fat dry milk and dietary calcium was increased to 1.2%; and a high dairy group in which 50% of the protein was replaced by non-fat dry milk, increasing calcium to 2.4%. Food intake and spillage was measured daily, and animals were weighed weekly. At the conclusion of the 6 week feeding period, animals were killed by exsanguination under isofluorane anesthesia, and blood was collected via cardiac puncture for glucose and insulin measurements. Fat pads (epididymal, perirenal, abdominal, and subscapular) were dissected, immediately weighted, frozen in liquid nitrogen, and stored at −80° C. Fatty acid synthase activity and mRNA levels were measured in abdominal fat.

Core Temperature

Core temperature was used as an indirect metabolic index to determine whether any reduction in efficiency of conversion of good energy to body weight was accompanied by increased thermogenesis. Temperature was measured via a thermo-couple (Columbus Instruments, Columbus, OH). The probe was inserted a constant distance (1.8 cm) into the rectum of each animal. After stabilization (10 s), the temperature was recorded every 5 s for 30 s. All temperature measurements were made between 8:00 and 9:00 a.m.

Intracellular Calcium (Human Adipocytes)

Intracellular $Ca^{2+}$ was determined fluorometrically as described previously. Cells were washed with HEPES-buffered salt solution loaded with fura-2-acetoxymethyl ester (10 µM) for 45 minutes at 37° C. in the dark with continuous shaking. Cells were then rinsed three times, resuspended, and intracellular $Ca^{2+}$ was measured using dual excitation (340 and 380 nm)/single emission (510 nm) fluorometry. After the establishment of a stable baseline, the response to 1,25-$(OH)_2$-D or parathyroid hormone (10 pM-100 nM) or their respective vehicles was determined. Digitonin (25 µM) and Tris/EGTA (100 mM, pH 8.7) were used to for calibration to calculate the final intracellular $Ca^{2+}$.

Lipolysis

Adipocytes were incubated for 4 hours in the presence or absence of forskolin (1 µM), and glycerol release into the culture medium was measured to assess lipolysis. Glycerol release data was normalized for cellular protein.

Fatty Acid Synthase Activity and mRNA Levels

Immediately after death, adipose tissue was isolated and fatty acid synthase activity was measured in cytosolic extracts by measuring the oxidation rate of NADPH. Enzyme activity was protein corrected using Coomassie blue dye.

Total RNA was extracted by cesium chloride density gradient, electrophoresed, subjected to Northern blot analysis, and hybridized with a radiolabeled rat cDNA probe for fatty acid synthase using standard methods. Autoradiographs were quantitated densitometrically, and all blots were stripped and reprobed with β-actin as a loading control.

Statistical Analysis (In Vitro and Animal Data)

All data are expressed as mean±SD. Data were evaluated for statistical significance by one-way analysis of variance (ANOVA) or t test, depending on the number of comparisons made. All data sets with multiple comparisons were analyzed via ANOVA, followed by separation of significantly different group means via test the least significant difference using SPSS-PC (v. 8.0).

NHANES III Analysis

To determine whether the animal observations are relevant in defining a role for dietary calcium in modulating body composition at the population level, an analysis of the National Health and Nutrition Examination Survey (NHANES III) data set was conducted. This large cross-sectional survey conducted between 1988 and 1994 followed a complex, four-stage probability sampling scheme designed to represent the entire U.S. civilian noninstitutionalized population over the age of 2 months. Only adults completing all three phases of the study (interview, physical examination, and laboratory examination) were included in this data analysis: respondents were excluded from this analysis if they could not provide complete, usable body composition/anthropometric data (e.g., amputees and individuals wearing casts), used insulin, or were pregnant, recently pregnant, or currently breast-feeding. Body composition was assessed using the anthropometric and bioelectrical impedance data collected during the physical examination, with percent body fat calculated using the regression equations derived by Segal.

Odds ratios for percent body fat and corresponding 95% confidence intervals were estimated by multiple logistic regression analysis with a Roust variance estimation method using SUDAAN (Shah, et al., SUDAAN User's Manual, Release 7.0 (1996)). Point estimates for all parameters were weighted to reflect the population distribution of each; variances were calculated using SUDAAN to take the complex sampling design into account. Analyses were conducted separately for men and women, and all odds ratios were adjusted for age by including age in the model as a continuous variable. Other covariates included in the model were caloric intake, race/ethnicity, and activity level. Characteristics of the study sample are shown in Tables 1 and 2.

TABLE 1

Characteristics of NHANES III Study sample[a]

|  | Women (n = 380) | Men (n = 7114) |
|---|---|---|
| Age (years) | 28.7 ± 0.4 | 43.5 ± 0.44 |
| Body mass index (kg/m$^2$) | 25.7 ± 0.4 | 26.6 ± 0.11 |
| Body fat (%) | 32.7 ± 0.6 | 25 ± 0.2 |
| Calcium intake (mg/day) | 720 ± 52 | 965 ± 15 |
| Dairy product consumption (monthly frequency) | 54.7 ± 3 | 51.4 ± 1 |
| Energy intake (kcal/day) | 1896 ± 68 | 2656 ± 28 |
| Dietary fat (g/day) | 74 ± 4 | 102 ± 2 |

[a] All data presented as mean ± SEM.

TABLE 2

Quartiles of body fat for women and men in the NHANES III Study[a]

| | % Body fat | |
|---|---|---|
| Quartile | Women | Men |
| 1 | 22.82 ± 0.45 | 15.47 ± 0.14 |
| 2 | 30.54 ± 0.17 | 22.83 ± 0.06 |
| 3 | 34.85 ± 0.18 | 27.55 ± 0.06 |
| 4 | 42.49 ± 0.44 | 34.08 ± 0.11 |

[a] Population (mean ± SEM).

Results

Figure 2:
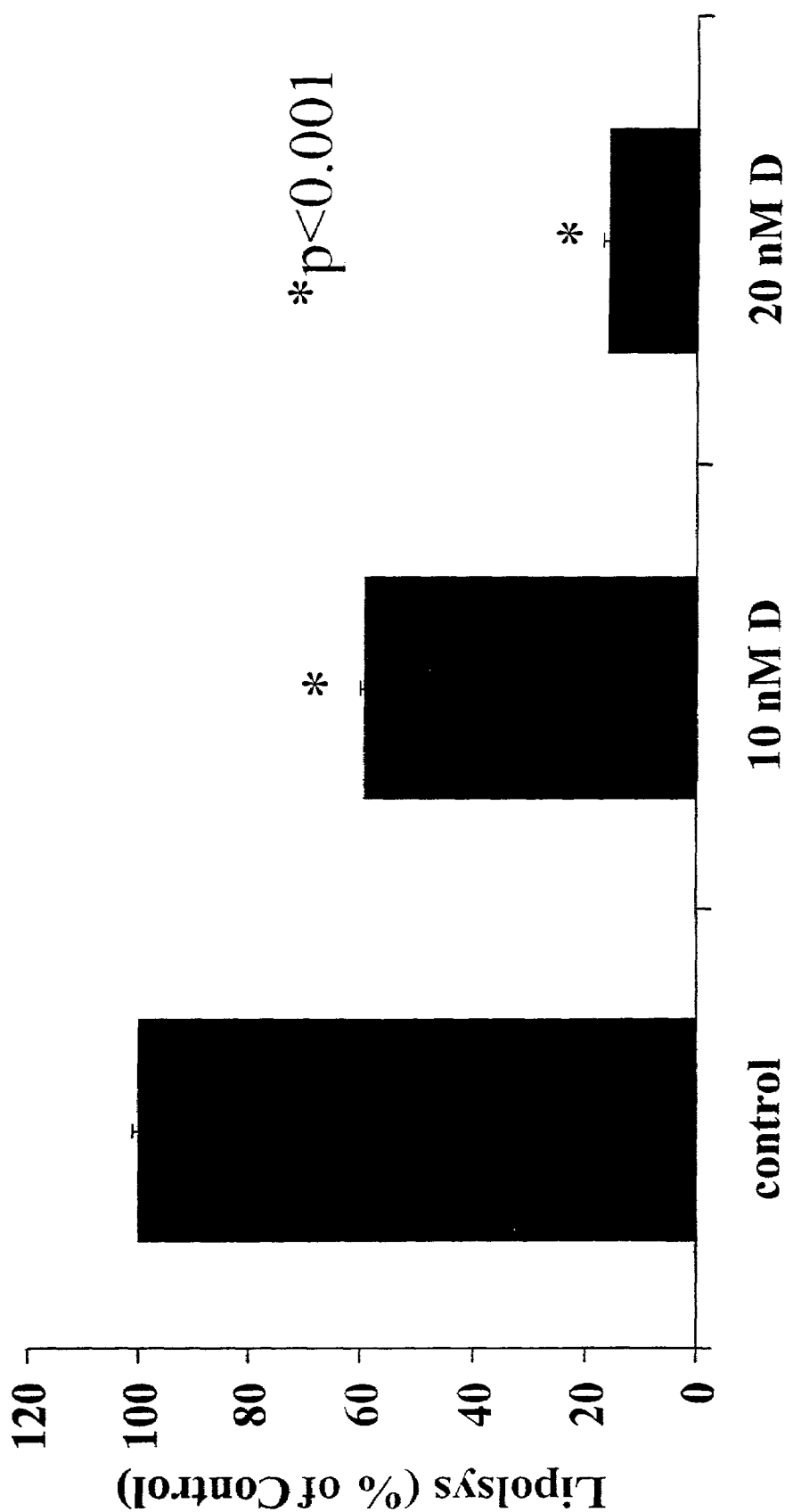
FIG. 2 depicts the effects of $1,25(OH)_2-D$ on forskolin-stimulated lipolysis in human adipocytes. Forskolin treatment resulted in a ~two-fold increase in glycerol release; data shown are normalized to 100% for the forskolin-treated group. (n=6/group; P<0.001).

FIG. 1 demonstrates that both 1,25-$(OH)_2$-D and parathyroid hormone (PTH) stimulate significant, sustained increases in intracellular $Ca^{2+}$ in primary cultures of human adipocytes (P<0.001: $EC_{50}$~50 pM for 1,25-$(OH)_2$-D and ~10 nM for PTH). 1,25-$(OH)_2$-D treatment also resulted in marked (83%) inhibition of forskolin-stimulated lipolysis (P<0.001) in human adipocytes (FIG. 2). PTH treatment exerted little effect on lipolysis (data not shown) despite its stimulation of an intracellular $Ca^{2+}$ response, most likely as a result of an accompanying activation of adenylate cyclase.

Figure 3:
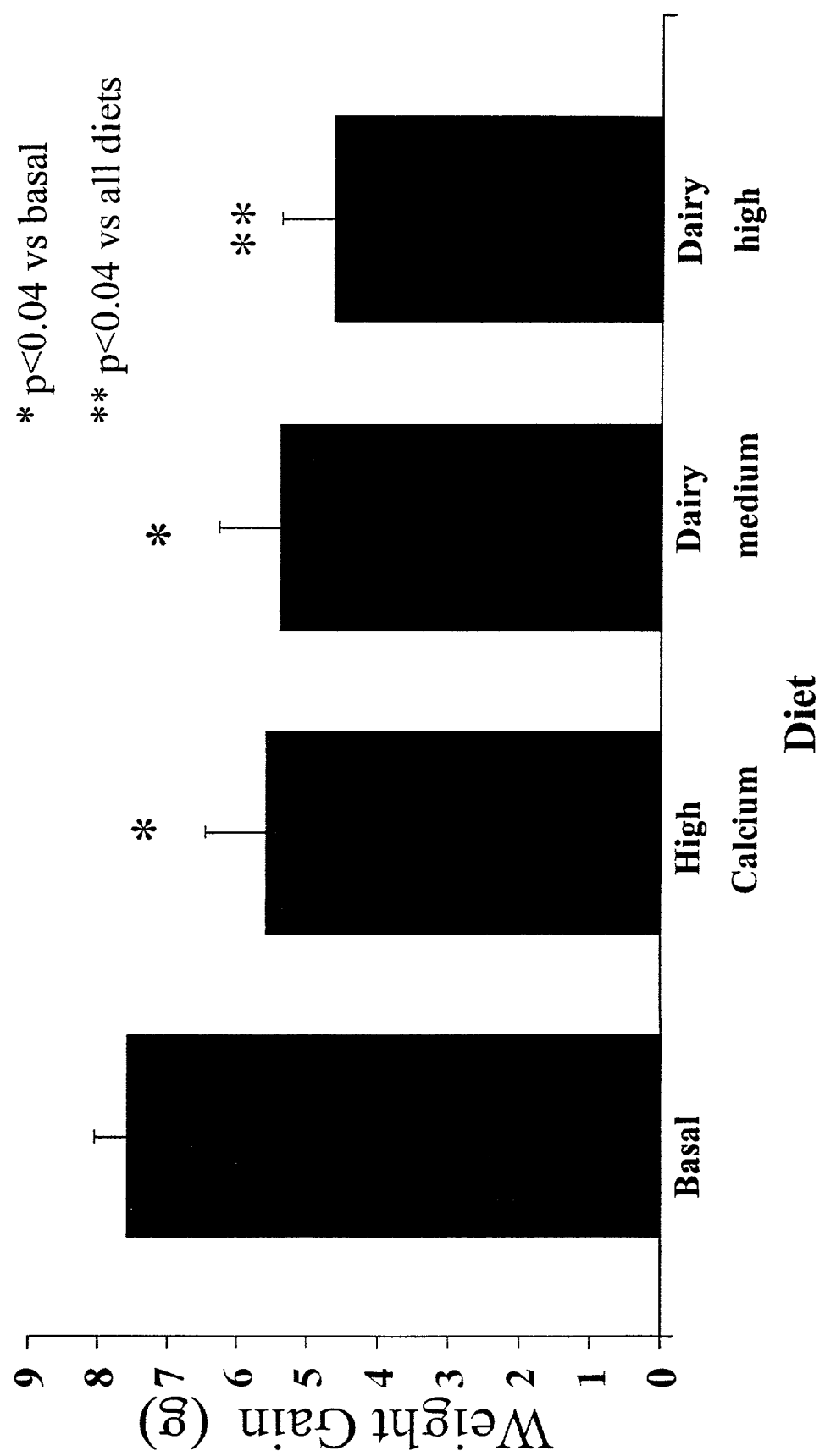
FIG. 3 illustrates the effects of calcium and dairy products on 6 wk weight gain in transgenic mice expressing agouti in adipose tissue under the control of the aP2 promoter.
Figure 4:
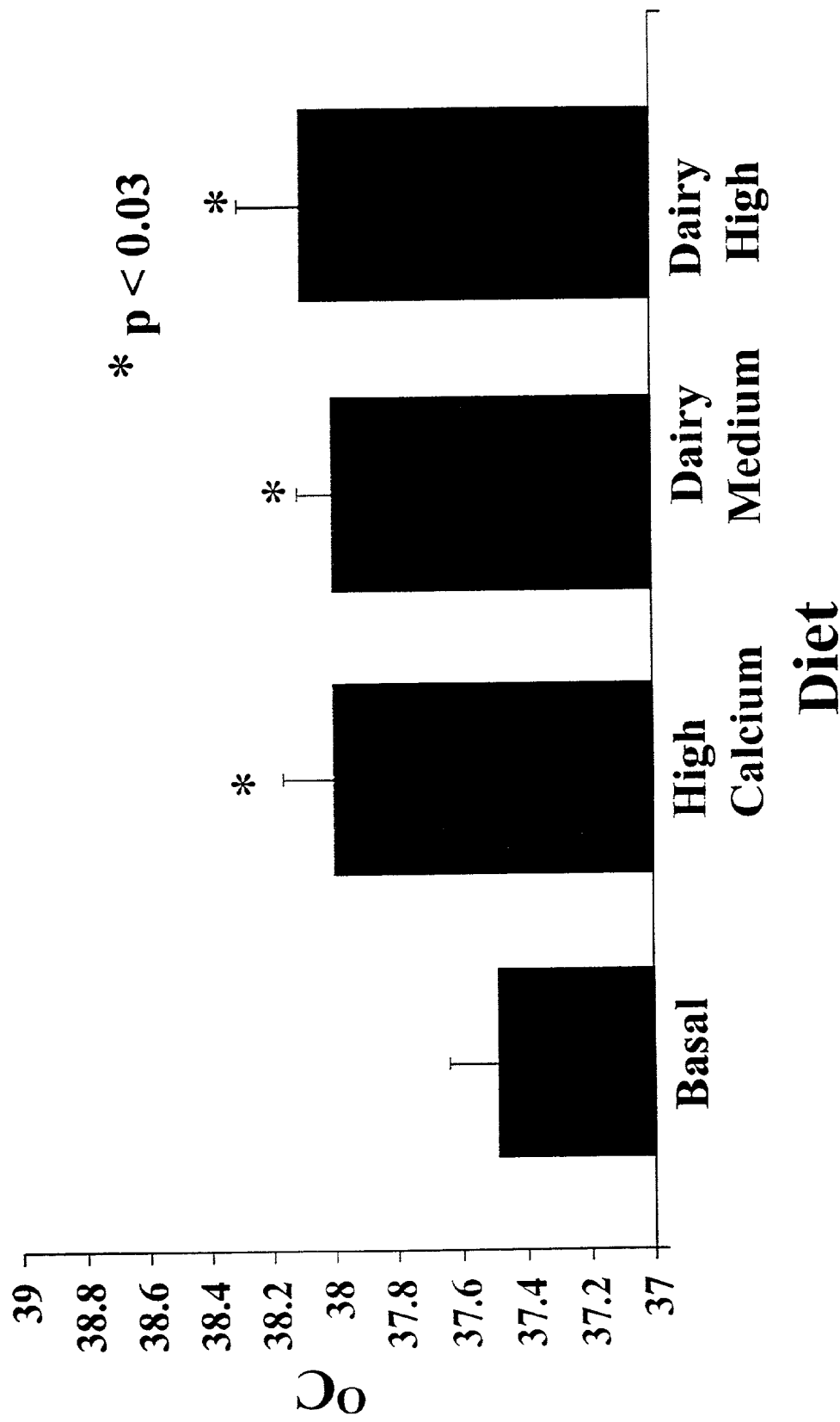
FIG. 4 depicts the effects of calcium and dairy products on core temperature in transgenic mice expressing agouti in adipose tissue under the control of the aP2 promoter.

Treatment of aP2-transgenic-agouti mice with the high fat/high sucrose basal diet resulted in a weight gain of 24%, which was reduced by 26 and 29% by the high calcium and medium dairy diets, respectively (P<0.04), and further reduced by 39% by the high dairy diet (P<0.04; FIG. 3). These differences occurred despite the lack of any difference in food intake. Measurement of core temperature, an indirect metabolic index, reflected these observations, with ~0.5° C.

increases in core temperature in response to all three high calcium diets (P<0.03; FIG. 4). This increase, coupled with the lack of difference in food intake, is indicative of a shift in efficiency of energy metabolism from energy storage to thermogenesis.

Figures 5A, 5B, 5C:
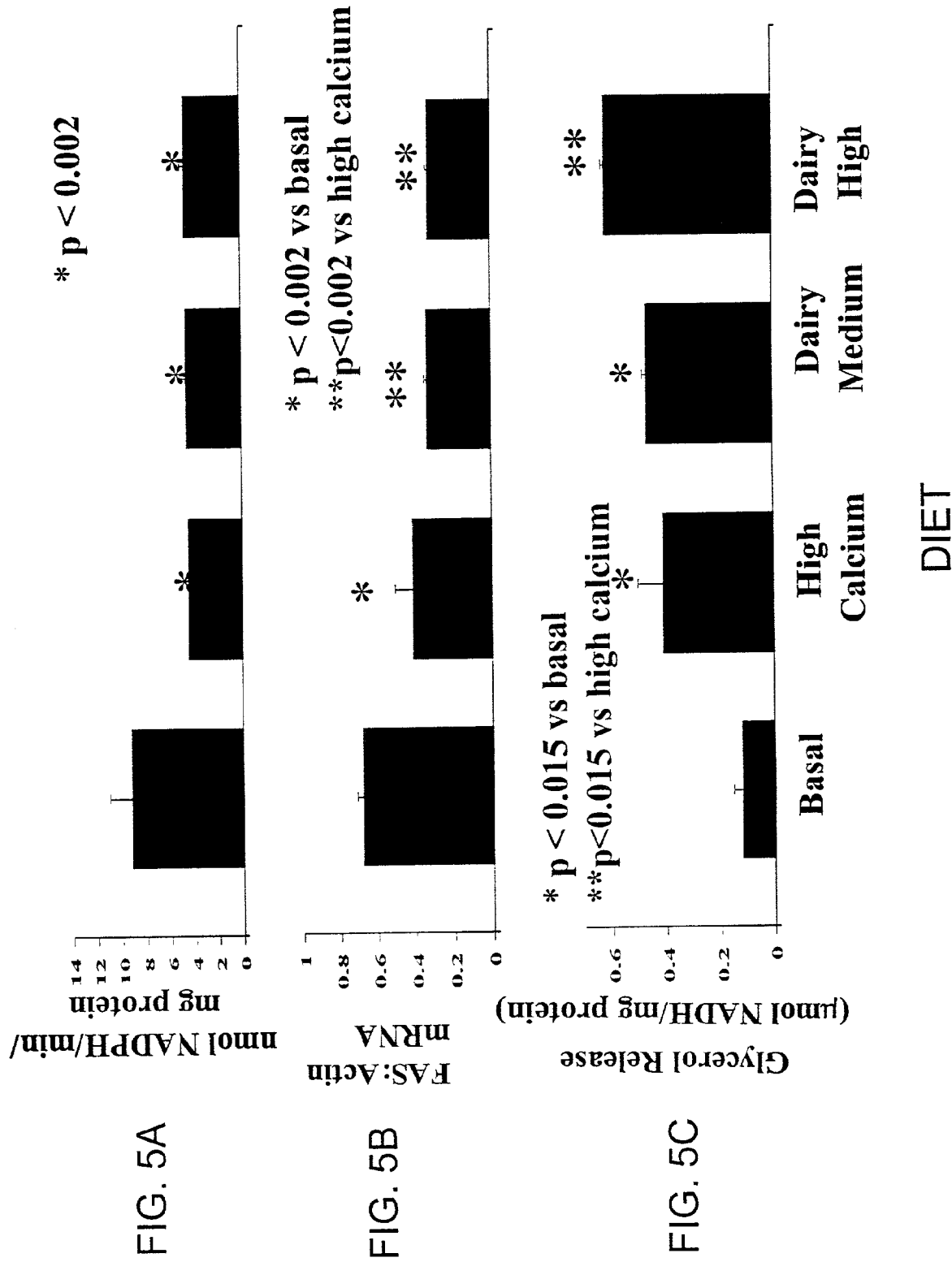
FIGS. 5A-C illustrate the effects of calcium and dairy products on adipocyte fatty acid synthase activity (upper panel), fatty acid synthase mRNA (middle panel) data are expressed as fatty acid synthase (FAS:actin ratio) and lipolysis in transgenic mice expressing agouti in adipose tissue under the control of the aP2 promoter. Data are expressed as mean±standard deviation (n=10/group). Statistical significance is as indicated in each panel.

This shift in energy metabolism was evident in studies of fatty acid synthase, a key enzyme in de novo lipogenesis that is highly sensitive to regulation by nutrients and hormones. The basal diet caused a 2.6-fold increase in fatty acid synthase activity, and this effect was markedly attenuated by all three high calcium diets (P<0.002; FIG. 5A). The diets caused corresponding decreases in adipocyte fatty acid synthase mRNA, with a 27% reduction on the high calcium diet and a 51% reduction on the medium and high dairy diets (P<0.01; FIG. 5B). Adipocyte lipolysis responded to dietary manipulations in an inverse fashion to the fatty acid synthase responses. The basal diet caused a marked (67%) suppression of lipolysis (P<0.0001); however, lipolysis was stimulated 3 to 5.2-fold by the high calcium diets (P<0.015; FIG. 5C), with greater effects from the high dairy diets than from the high calcium diet. Assessment of fat pad mass after 6 wk of dietary treatment provides further support for these findings. Table 3 demonstrates that all three high calcium diets caused a 36% reduction in mass of the epididymal, abdominal, perirenal, and subscapular adipose tissue compartments (P<0.001). Epididymal and subscapular fat pad mass was reduced by ~50% by all three diets, whereas the abdominal fat pads exhibited greater decreases on the medium and high dairy diets than on the high calcium diet (P<0.001; Table 3).

TABLE 3

Effects of calcium and dairy products on fat pad mass in transgenic mice expressing Agouti in adipose tissue under control of the aP2 promoter[a]

| | Basal | High Calcium | Medium dairy | High dairy |
|---|---|---|---|---|
| Abdominal (g) | 2.239 ± 0.109 | 1.807 ± 0.082* | 1.661 ± 0.127** | 1.680 ± 0.113** |
| Perirenal (g) | 1.675 ± 0.124 | 1.271 ± 0.098* | 1.172 ± 0.128* | 1.052 ± 0.094* |
| Epididymal (g) | 0.198 ± 0.036 | 0.110 ± 0.017* | 0.110 ± 0.014* | 0.097 ± 0.015* |
| Subscapular (g) | 1.592 ± 0.318 | 0.680 ± 0.069* | 0.663 ± 0.068* | 0.639 ± 0.087* |
| Sum[b] (g) | 5.703 ± 0.548 | 3.649 ± 0.238* | 3.705 ± 0.276* | 3.787 ± 0.251* |

[a]Data expressed as mean ± deviation.
[b]Sum of abdominal, perirenal, epididymal, and subscapular fat pads.
*P < 0.001 vs. basal.
**P < 0.001 vs. high calcium.

Figures 6A, 6B:
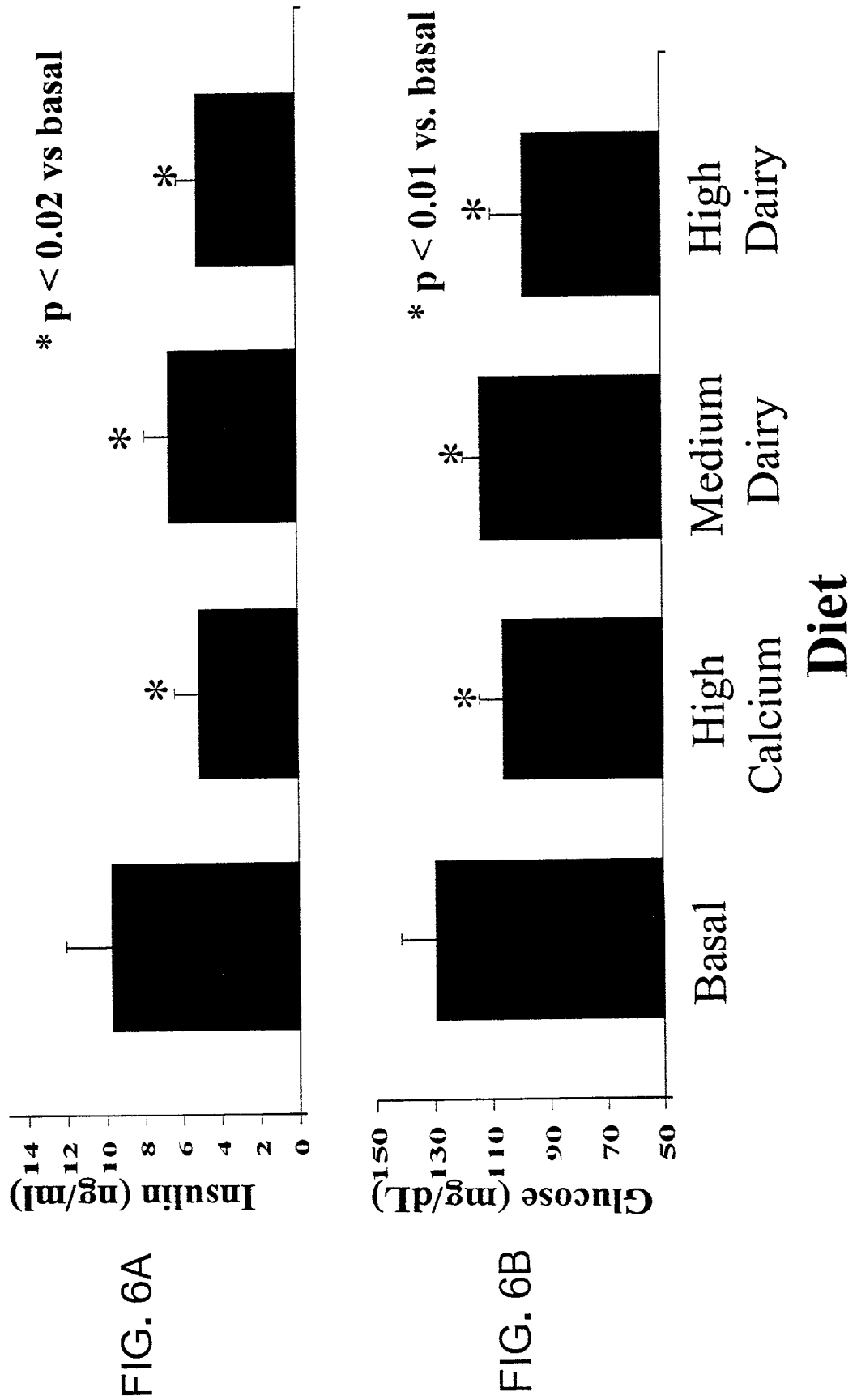
FIGS. 6A-B depict the effects of calcium and dairy products on fasting plasma glucose and insulin levels in transgenic mice expressing agouti in adipose tissue under the control of the aP2 promoter. The top panel depicts insulin and the bottom panel depicts glucose.

Serial measurements of plasma glucose and insulin demonstrate a diabetogenic effect of the basal high fat/high sucrose/low calcium diet, with an increase in fasting glucose from 98±10 to 130±11 mg/dl (P<0.02) and a corresponding degree of compensatory hyperinsulinemia. These increases were attenuated by the high calcium and medium dairy diets and prevented by the high dairy diet (FIG. 6).

Table 4 summarizes the NHANES III data analysis. After controlling for energy intake, activity level, age, race, and ethnicity, the odds ratio of being in the highest quartile of body fat was markedly reduced from 1.00 for the first quartile of calcium intake to 0.75, 0.40, and 0.16 for the second, third, and fourth quartiles, respectively (multiple $R^2$=0.20; P=0.0009), in adult women. Similarly, the regression model for males demonstrated an inverse relationship between calcium and dairy intakes and body fat (multiple $R^2$=0.40; P=0.0006), although a comparable dose-responsive reduction in relative risk (odds ratio) by quartile of calcium intake was not evident from the model.

TABLE 4

Effects of dietary calcium, and dairy intake on the risk of being in the highest quartile of body fat for women[a]

| Quartile of calcium and dairy consumption | Calcium intake (mg/day: mean ± SEM) | Dairy consumption (servings, month: mean ± SEM) | Odds ration of being in the highest body fat quartile |
|---|---|---|---|
| 1 | 255 ± 20 | 14.4 ± 1.9 | 1.00 |
| 2 | 484 ± 13 | 38 ± 1.3 | 0.75 (0.13, 4.22)[b] |
| 3 | 773 ± 28 | 57.2 ± 1.0 | 0.40 (0.01, 3.90)[b] |
| 4 | 102.8 ± 3.6 | 1346 ± 113 | 0.16 (0.03, 0.88)[b] |

[a]Model is controlled for race/ethnicity and activity level, with age and caloric intake as continuous covariates.
[b]95% Confidence interval in parenthesis

Example 2

Effects of Dietary Calcium on Adipocyte Extracellular Calcium, Lipid Metabolism, and Weight and Fat Reduction

Materials and Methods

Animals and Diets aP2-agouti transgenic (aP2-a) mice were used as an animal model in this study. The characterization of these animals has been described previously (Mynatt, et al. (1997)). These transgenic mice express normal agouti protein specifically in adipose tissue under the control of the aP2 promoter (Mynatt, et al. (1997)), similar to the adipocyte-specific human pattern of agouti expression. These mice are useful as an animal model for the study of diet-induced obesity study, as they are not obese on a standard AIN 93-G diet, but become obese in response to hyperinsulinemia induced by either exogenous insulin administration (Mynatt, et al. (1997)) or high sucrose diet (Zemel, et al. (1999)).

This study was divided into two 6-week stages. In the first stage, 60 6-week-old male aP2 mice were placed on a modified AIN 93-G diet with suboptimal calcium (0.4%), sucrose as the sole carbohydrate source and lard added to increase fat to 25% of energy. To evaluate this low calcium/high fat/high sucrose diet-induced obesity in these animals, we monitored the body weight was monitored every 5 days and 8 representative mice were euthanized for measurement of fat pad mass and adipocyte $[Ca^{2+}]_i$ at the end of first 6 week-basal diet feeding. In the second 6-week stage, the rest of mice that exhibited diet-induced obesity were randomly assigned to five groups. One group was continued ad lib on the same low calcium (0.4%) diet with no modification, while the other four groups were maintained with energy restriction (70% of ad lib) as follows. The mice in basal restriction group were placed on the basal low calcium (0.4%) diet with Kcal-restriction. A high calcium energy restricted group received the basal diet supplemented with calcium increased to 1.2%. Two additional groups, termed medium dairy and high dairy, were fed modified basal diet in which either 25 or 50% of protein was replaced by non-fat dry milk, with total dietary calcium increased to 1.2 or 2.4%, respectively. Diet was administrated daily and body weight was monitored every five days. At the end of second stage, all mice were euthanized with beuthanasia (concentrated pentobarbital with phenytoin) and blood was obtained via cardiac puncture for insulin and glucose measurement. Fat pads (epididymal, perirenal, abdominal and subscapular) were dissected, immediately weighed, frozen in liquid nitrogen, and stored at −80° C. Fatty acid synthase activity and mRNA levels were measured in abdominal fat.

Core Temperature

Core temperature was used as an indirect metabolic index to determine if dietary calcium regulates energy metabolism associated with increased thermogenesis, an important contribution to energy expenditure. Temperature was measured via a thermocouple (Columbus Instruments, Columbus, Ohio) weekly (Kim, et al. (1996)). The probe was inserted a constant distance (1.8 cm) into the rectum of each mouse. After stabilization (10 seconds), the temperature was recorded every 5 seconds for 30 seconds. All core temperature measurements were performed between 8:00 and 9:00 A.M.

Mouse Adipocyte Intracellular $Ca^{2+}$ ($[Ca^{2+}]_i$) Measurement

Isolated mouse adipocytes were prepared from mouse abdominal fat depots as previously described (Shi, et al. (1999)) with slight modification. Briefly, adipose tissue was first washed several times with Hank's Balanced Salt Solution, minced into small pieces and digested with 0.8 mg/ml type I collagenase in a shaking water bath at 37° C. for 30 min. Adipocytes were then filtered through a sterile 500 µm nylon mesh and cultured in Dulbecco's Modified Eagle's Medium (DMEM) supplemented with 1% fetal bovine serum (FBS). Cells were cultured in suspension and maintained in a thin layer at the top of culture media for two hours for cell recovery.

$[Ca^{2+}]i$ in isolated mouse adipocytes was measured using a fura-2 dual wavelength fluorescence imaging system. Prior to $[Ca^{2+}]i$ measurement, adipocytes were pre-incubated in serum-free medium for 2 hrs and rinsed with Hepes Balanced Salt Solution (HBSS) containing the following components (in mmol/L): NaCl 138, $CaCl_2$ 1.8, $MgSO_4$ 0.8, $NaH_2PO_4$ 0.9, $NaHCO_3$ 4, glucose 5, glutamine 6, Hepes 20, and bovine serum albumin 1%. Adipocytes were loaded with fura-2 acetoxymethyl ester (AM) (10 µmol/L) in the same buffer for 1 hr at 37° C. in a dark incubator with 5% $CO_2$. To remove extracellular dye, adipocytes were rinsed with HBSS 3 times and then post-incubated at room temperature for an additional 30 min for complete hydrolysis of cytoplasmic fura-2 AM. A thin layer of adipocytes was plated in 35 mm dished with glass coverslips (P35G-0-14-C, MatTek Corporation). The dishes with dye-loaded cells were mounted on the stage of Nikon TMS-F fluorescence inverted microscope with a Cohu 4915 CCD camera. Fluorescent images were captured alternatively at excitation wavelength of 340 and 380nM with an emission wavelength of 520 nM. $[Ca^{2+}]i$ was calculated using a ratio equation as described previously(Grynkiewicz, et al. (1985)).

Fatty Acid Synthase (FAS) Activity Assay

FAS activity was determined spectrophotometrically in crude cytosolic extracts of mouse adipose tissue as previously described (Jones, et al. (1997)). Mouse abdominal fat pads were homogenized in 250 mmol/L sucrose solution containing 1 mmol/L ethylenediamine-tetraacticacid (EDTA), 1 mmol/L dithiothreitol (DTT), and 100 µmol/L phenylmethylsulfonyl fluoride (PMSF) (pH 7.4). Homogenate was centrifuged at 18,500×g for 1 hr and the infranatant was used for measuring oxidation rate of NADPH.

Lipolysis Assay

Following the sacrifice, mouse perirenal adipose tissue was immediately dissected and incubated for four hours. Glycerol released into the culture medium was determined as an indicator of lipolysis, using a one-step enzymatic fluorometric method as previously described (Boobis, et al. (1983)).

Northern Blot Analysis

Northern blot analysis was conducted as described (Shi, et al. (1999)). Total RNA from mouse abdominal adipose tissue was extracted using $CsCl_2$ density centrifugation, run in 1% agarose gel and transferred to nylon membrane (New England Nuclear, Boston, Mass.). The membrane was hybridized with uncoupling protein 2 (UCP2) or FAS cDNA probes that were radiolabeled using a random primer method. Unbound probe was removed by rinsing the membrane with 2×SSC/0.1% SDS for 30 min at room temperature and 0.1× SSC/0.1% SDS for 45 min at 55° C. Finally, the membrane was exposed to X-ray film (New England Nuclear, Boston, Mass.) at −80° C. All membranes were stripped and reprobed with β-actin as loading control.

Statistical Analysis

All data are expressed as mean±SE and evaluated for statistical significance by one way Analysis of Variance (ANOVA) using SPSS (SPSS Inc, Chicago, Ill.). A p value <0.05 is considered significant.

Results

Figure 7A:
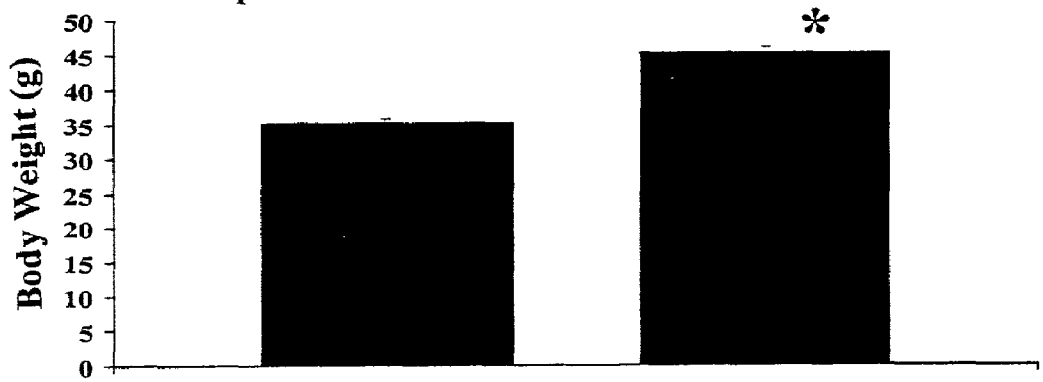
FIGS. 7A-C show the effects of 6-week consumption of basal low calcium (0.4%), high fat, high sucrose diet on body weight (top panel), total fat pad mass (middle panel) and basal adipocyte $[Ca^{2+}]_i$ lower panel) in aP2-agouti transgenic mice. Data are expressed as mean±SE (n=8). *p<0.001 vs. before administration.
Figure 7B:
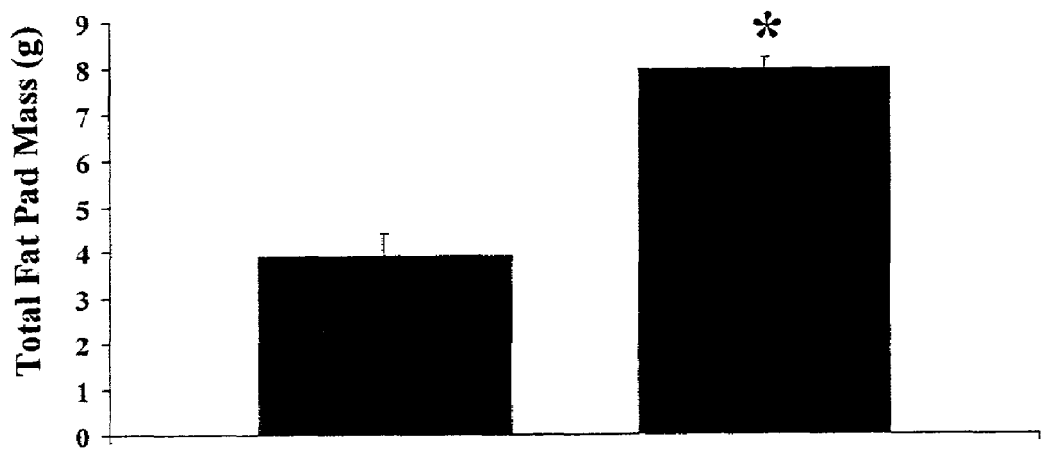
Figure 7C:
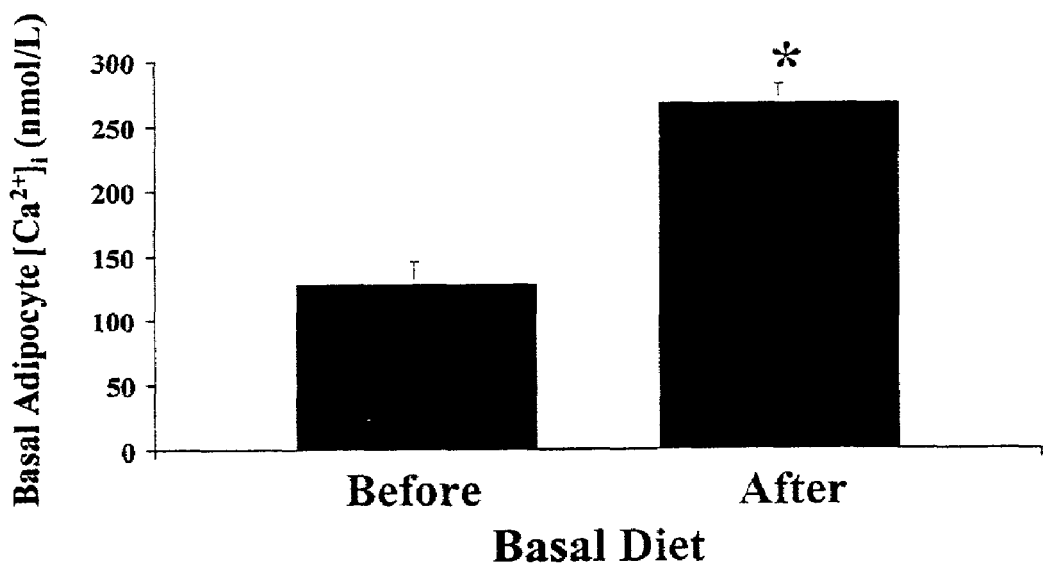

To establish the animal model of diet-induced obesity in aP2-agouti transgenic (aP2-a) mice, mice were placed on low calcium (0.4%)/high fat/high sucrose diet for 6 weeks. Administration of aP2-a mice with this diet resulted in a 2-fold increase in adipocyte $[Ca^{2+}]_i$ (128±18 vs. 267±15 nM, p<0.001, lower panel, FIG. 7), with a corresponding body weight gain of 27% (p<0.001, upper panel, FIG. 7) and two fold increase in total fat pad mass (P<0.001, middle panel, FIG. 7), demonstrating that diet-induced dysregulation of adipocyte $[Ca^{2+}]_i$ is associated with increased adiposity in aP2-a mice.

Figure 8A:
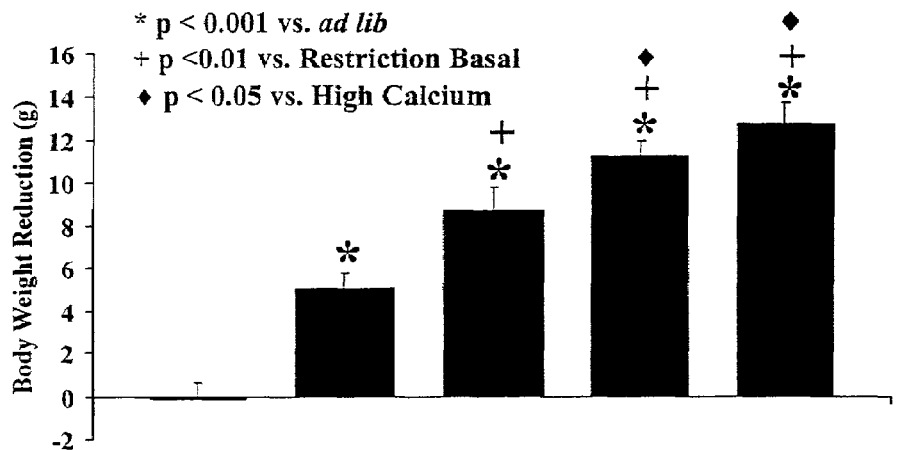
FIGS. 8A-C show the effects of 6-week administration of high calcium diets on weight reduction (FIG. 8A, upper panel), fat pad mass (FIG. 8B, middle panel) and basal adipocyte $[Ca^{2+}]_i$ (FIG. 8C, lower panel) in energy-restricted (70% of ad lib) aP2-agouti transgenic mice. Data are expressed as mean±SE (n=8).
Figure 8B:
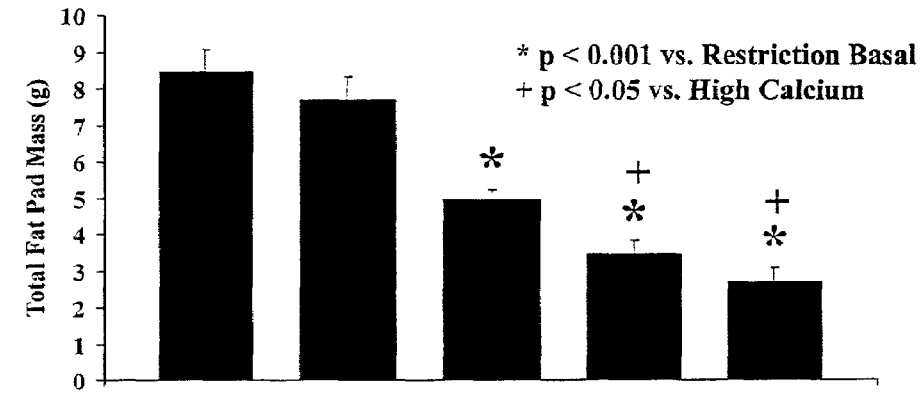
Figure 8C:
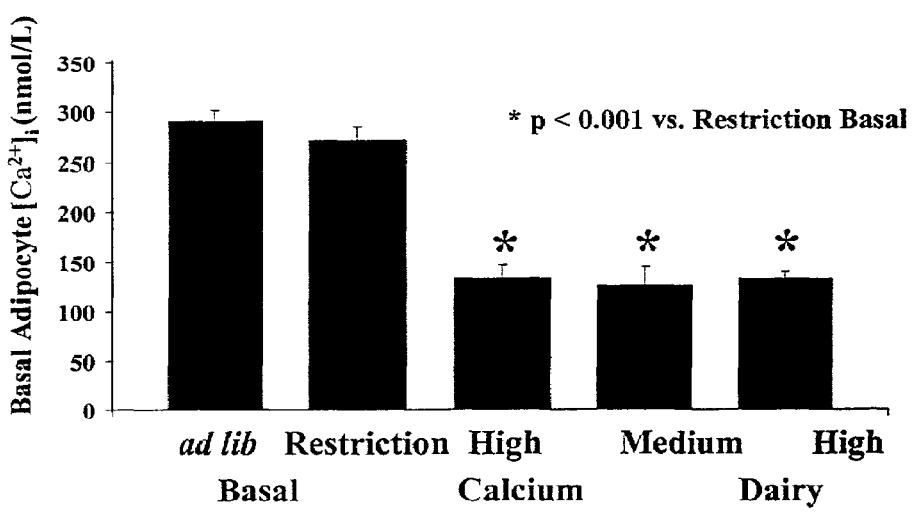

The role of dietary calcium in facilitating weight loss in calorically restricted obese aP2-a mice was evaluated. These obese aP2-a mice were maintained either on the same low calcium basal diet ad lib or on the Kcal-restricted (70% of ad lib) diets supplemented with or without dairy or $CaCO_3$ as dietary calcium supplementary sources. FIG. 8 illustrates that all three calcium diets, including high calcium diet (1.2% $Ca^{2+}$ derived from $CaCO_3$), medium dairy diet (1.2% $Ca^{2+}$ derived from non-fat dry milk replacing 25% of protein) and high dairy diet (2.4% $Ca^{2+}$ derived from non-fat dry milk replacing 50% of protein), caused a 50% decrease in adipocyte $[Ca^{2+}]$, (P<0.001, FIG. 8), while $[Ca^{2+}]_i$ in adipocytes from mice maintained on the Kcal-restricted basal low calcium diet remained at the same elevated level as that of ad lib animals.

An examination was conducted as to whether a dietary calcium-induced decrease in adipocyte $[Ca^{2+}]_i$ facilitated the body weight loss and fat pad mass reduction. As shown in FIG. 8, energy restriction resulted in a body weight loss by 11% (P<0.001, FIG. 8), compared to ad lib group. However, markedly greater weight reductions of 19, 25, 29% were observed in the high calcium, medium and high dairy groups, respectively (P<0.01 vs. basal energy-restricted group, FIG. 8). Consistent with this, energy restriction caused an only 8% decrease in fat pad mass, compared to basal diet ad lib group, while the high calcium diet caused a 42% decrease (P<0.001, FIG. 8), which was further reduced by 60 and 69% by the medium and high dairy diets (P<0.001 vs. basal energy-restricted group, FIG. 8), respectively.

Figure 9A:
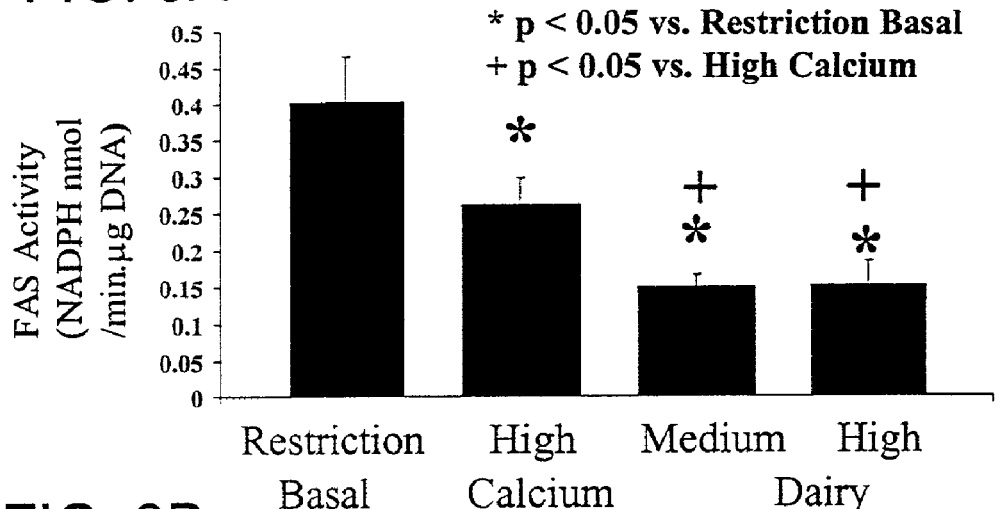
FIGS. 9A-C show the effects of 6-week administration of high calcium diets on fatty acid synthase activity (FIG. 9A, upper panel), fatty acid synthase mRNA (FIG. 9B, middle panel) and lipolysis (FIG. 9C, lower panel) in energy-restricted (70% of ad lib) a Pe-agouti transgenic mice. Glycerol release is used to measure lipolysis. Data are expressed as mean±SE (n=8).
Figure 9B:
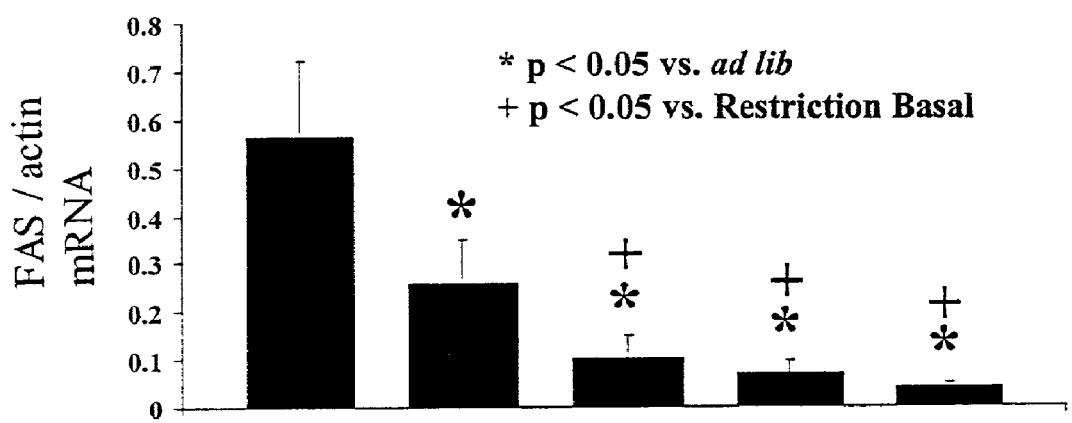
Figure 9C:
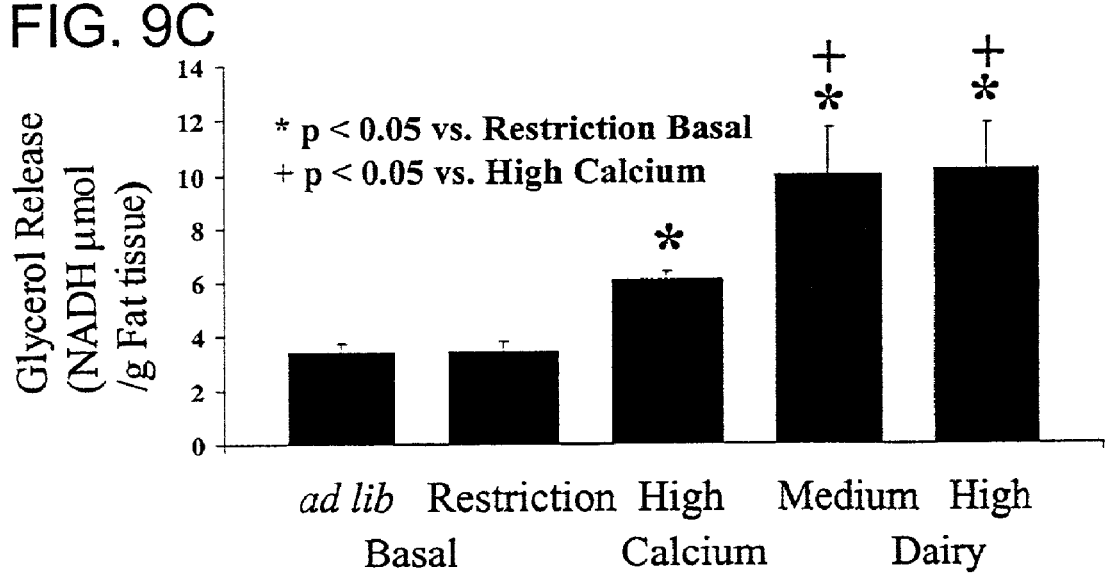

FIG. 9 demonstrates that the high calcium diet caused a 35% decrease in fatty acid synthase (FAS) activity (P<0.05 vs. basal energy-restricted group), which was further reduced by 63 and 62% by the medium and high dairy diets (P<0.05), respectively. Similarly, the three high calcium diets caused corresponding decreases in adipocyte FAS mRNA, with 61%, 72% and 81% reductions on high calcium, medium dairy and high dairy diets, respectively (P<0.05 vs. basal energy-restricted group, FIG. 9). Increasing dietary calcium caused a corresponding increase in lipolysis. Although the basal energy restricted diet did not affect adipocyte lipolysis, the high calcium diet caused 77% stimulation in lipolysis (P<0.05. FIG. 9), which was further increased by 2 fold in the medium and high dairy diet groups (P<0.05 vs. basal energy-restricted group, FIG. 9). Increased lipolysis, coupled with decreased lipogenesis, may represent a metabolic state in which the efficiency of energy metabolism is shifted from energy storage to energy expenditure.

Figure 10B:
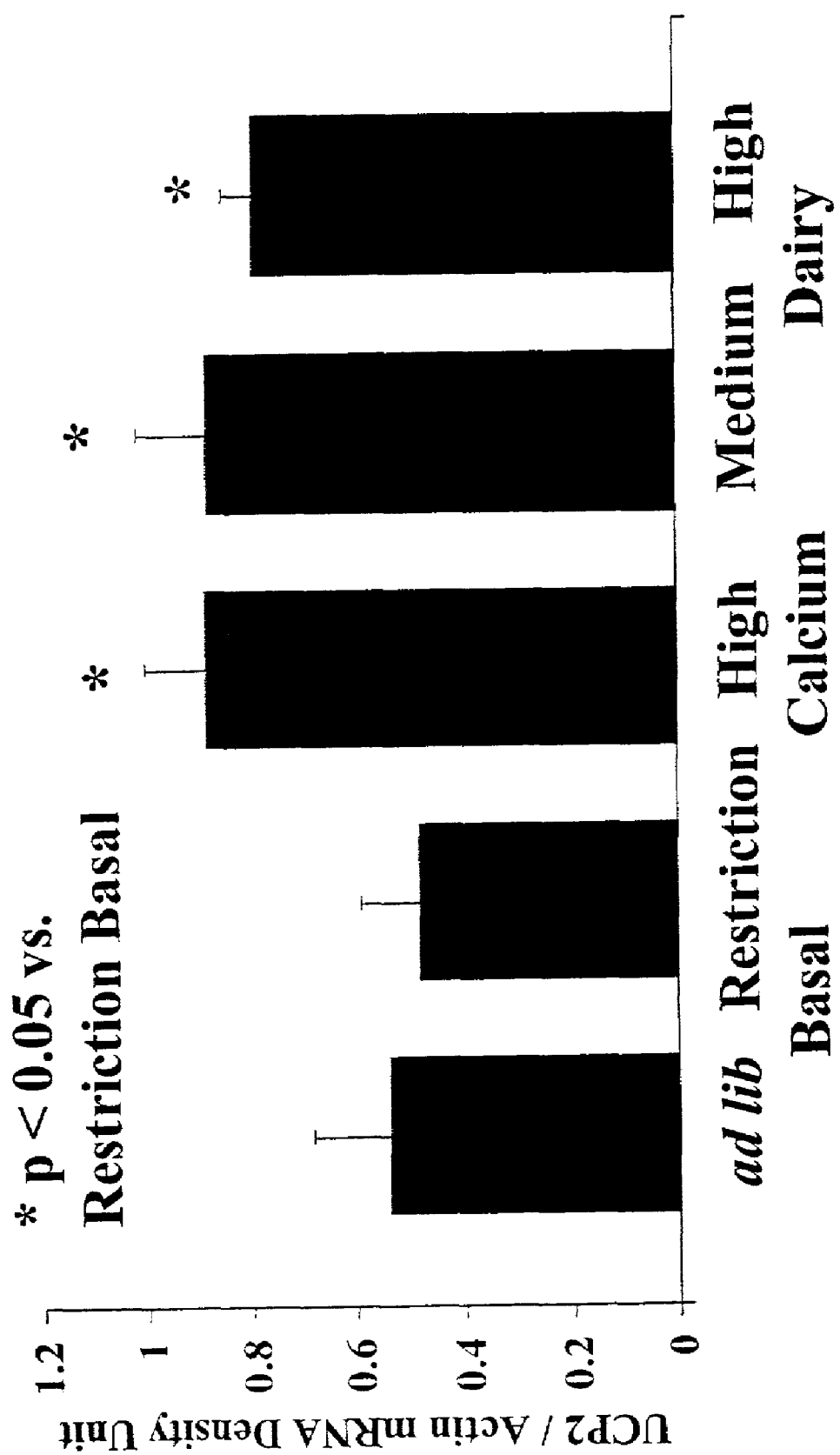

This shift in energy metabolism was further confirmed by dietary calcium-induced increase in core temperature. All three high calcium diets exerted stimulatory effects on core temperature, with 0.48° C., 0.57° C. and 0.67° C. increases on the high calcium, medium dairy and high dairy diets, respectively (P<0.05), while the basal energy restricted diet did not affect on core temperature. A possible physiological basis underlying the increased core temperature is that the expression of uncoupling protein 2 (UCP2), which has been implicated in thermogenesis (Fleury, et al. (1997); Gimeno, et al. (1997)), was up-regulated in white adipose tissue, with 80% increase on all three high calcium diets (P<0.05, FIG. 10). This demonstrates that dietary calcium may also modulate energy metabolism associated with thermogenesis. Accordingly, a coordinated up-regulation of lipolysis and down-regulation of lipogenesis, coupled with increased thermogenesis, may serve to shift the energy metabolism from energy storage to energy expenditure on high calcium diets.

Figure 11:
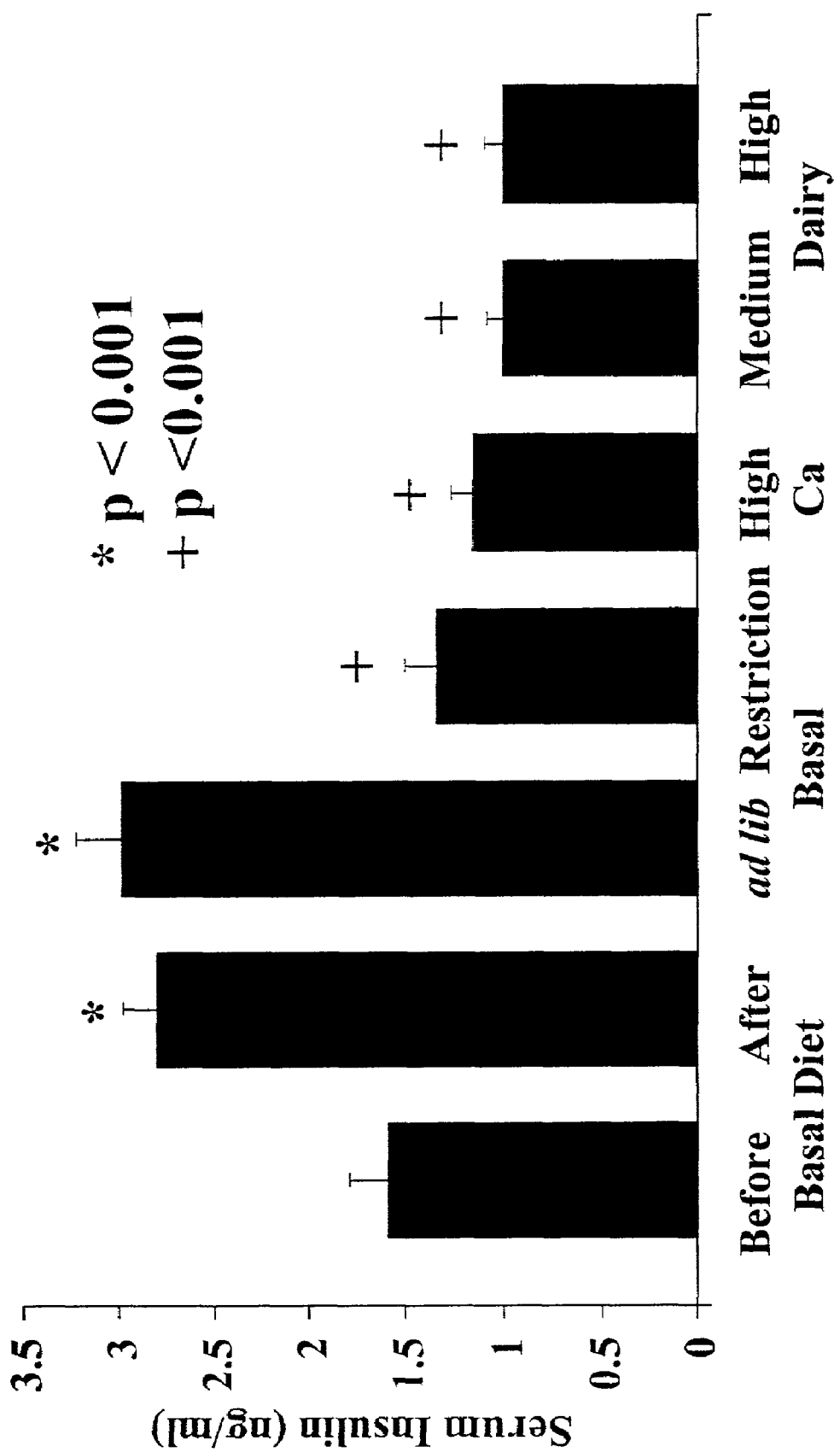
FIG. 11 shows the effects of dietary calcium on plasma insulin levels. Data are expressed as mean±SE (n=8). * p<0.001 vs. before basal diet treatment; +p<0.001 vs. ad libitum.

The basal low calcium diet exerted a hyperinsulinemic effect, with a 2-fold increase in plasma insulin levels (P<0.001, FIG. 11). The mice maintained on this basal diet ad lib exhibited sustained levels of hyperinsulinemia, while energy restriction per se reduced plasma insulin by approximately 50%. The high calcium diets did not further significantly affect insulin levels, although there was a non-significant trend towards further reductions (FIG. 11).

Example 3

Methods of Administering a High Calcium Diet

The subject invention provides methods useful in diagnosing, treating, and/or monitoring obesity. One method of the subject invention comprises the following steps:
1. determining the weight and, optionally, the height of an individual;
2. comparing the weight, or optionally the weight/height ratio, of the individual to established norms;
3. optionally, classifying the obesity of the individual;
4. optionally providing the individual with information relating to the benefits of maintaining a normal weight, or a normal weight/height ratio; and
5. providing the individual with a dietary plan containing high levels of calcium and, optionally printed matter disclosing the obesity-control benefits of a high calcium diet.

The subject invention also provides computer implemented methods of diagnosing, treating, and/or monitoring obesity. The methods of this embodiment of the subject invention can comprise the following steps:
1. determining the weight and, optionally, the height of an individual and inputting these values into a computer system;
2. optionally calculating the weight/height ratio of the individual;
3. comparing the weight, or optionally the weight/height ratio, of the individual to established norms contained in a weight and/or weight/height database available to the computer;
4. optionally classifying the obesity of the individual;
5. optionally providing the individual with information relating to the benefits maintaining a normal weight, or optionally a normal weight/height ratio; and
6. providing the individual a dietary plan containing high levels of calcium and, optionally printed matter disclosing the obesity-control benefits of a high calcium diet.
7. optionally monitoring the progress of the individual.

The subject invention also provides computer implemented methods of diagnosing, treating, and/or monitoring obesity over a communication network. The methods of this embodiment of the subject invention can comprise the following steps:
1. obtaining weight and, optionally, height data from an individual by input of the data on a web page;
2. optionally calculating the weight/height ratio of the individual in a computer connected to the communication network;
3. comparing the weight, or optionally the weight/height ratio, of the individual to established norms contained in a weight and/or weight/height database available to said computer;
4. optionally classifying the obesity of the individual;
5. optionally providing the individual with information relating to the benefits maintaining a normal weight, or optionally a normal weight/height ratio; and
6. providing the individual a dietary plan containing high levels of calcium and, optionally, information regarding the obesity-control benefits of a high calcium diet.

This method may further provide requesting verification that the weight and height values inputted by the individual are correct. The method may also provide the classification of obesity, information relating to the benefits maintaining a normal weight, or optionally a normal weight/height ratio, providing the individual a dietary plan containing high levels of calcium and/or information regarding benefits of a high calcium diet to the individual only at the request of the individual. The communication network maybe the Internet, an intranet, LAN, WAN, a real private network, or two or more computers connected electronically.

Example 4

1α,25-Dihydroxyvitamin $D_3$ Modulation of Human Adipocyte Metabolism

Materials and Methods

Culture of Human Adipocytes

A human adipocyte cell line and primary-cultured human adipocytes were both used as cell models in this study. The human adipocyte cell line was differentiated from human preadipocytes obtained from Zen-Bio Inc. (Research Triangle Park, N.C.). Human preadipocytes were inoculated in Dulbecco's Modified Eagle' Medium (DMEM)/Ham' F-10 medium (F-10) (1:1, v/v) containing 10% fetal bovine serum (FBS), 15mM Hepes and antibiotics at a density of 30,000 cells/cm². Confluent monolayers of preadipocytes were induced to differentiate with a standard differentiation medium consisting of DMEM/F-10 (1:1, v/v) medium supplemented with 15 mM Hepes, 3% FBS, 33 μM biotin, 17 μM pantothenate, 100 nM insulin, 0.25 mM methylisobutylxanthine (MIX), 1 μM dexamethasone, 1 μM BRL49653 and antibiotics. Preadipocytes were maintained in this differentiation medium for 3 days and subsequently cultured in adipocyte medium in which BRL49653 and MIX were withdrawn. Cultures were re-fed every 2-3 days (Shi, H., et al., "Role of intracellular calcium in human adipocyte differentiation," *Phyisol. Genomics*. (2000) pp. 75-82, vol. 3.).

Primary-cultured human adipocytes were derived from human subcutaneous adipose tissue obtained from patients undergoing abdominal plastic surgery with no known history of metabolic disorders. This protocol was approved by the Institutional Review Board for Human Subjects and the Committee for Research Participation of the University of Tennessee. Adipocytes were isolated according to the teachings of (Shi, H., et al., "Role of the sulfonylurea receptor in regulating human adipocyte metabolism," *FASEB. J.* (1999) pp. 1833-38, vol. 13.). Briefly, adipose tissue was first washed several times with Hank's Balanced Salt Solution, minced into small pieces and digested with 1 mg/ml type1 collagenase in a shaking water bath at 37° C. for 30 min. Adipocytes were then filtered through a sterile 500 μm nylon mesh and cultured in Dulbecco's Modified Eagle's Medium (DMEM) supplemented with 1% fetal bovine serum (FBS), 100 UI/ml penicillin, 100 μg/ml streptomycin and 50 μg/ml gentamicin. Cells were cultured in suspension and maintained in a thin layer at the top of culture media, which were changed every day. Cells were maintained viable and metabolically responsive under this culture condition for 7 days.

Human Adipocyte Intracellular $Ca^{2+}$ ($[Ca^{2+}]_i$) Measurement $[Ca^{2+}]i$ in human preadipocytes was measured using a fura-2 dual wavelength fluorescence imaging system (Shi, H., et al., "Role of intracellular calcium in human adipocyte differentiation," *Phyisol. Genomics*. (2000) pp. 75-82, vol. 3.). Preadipocytes were plated and differentiated in 35 mm dishes with glass coverslips (P35G-0-14-C, MatTek Corporation). Prior to $[Ca^{2+}]i$ measurement, cells were preincubated in serum-free medium overnight and rinsed with Hepes Balanced Salt Solution (HBSS) containing the following components (in mM): NaCl 138, $CaCl_2$ 1.8, $MgSO_4$ 0.8, $NaH_2PO_4$ 0.9, $NaHCO_3$ 4, glucose 5, glutamine 6, Hepes 20, and bovine serum albumin 1%.

Cells were loaded with fura-2 acetoxymethyl ester (AM) (10 μM) in the same buffer for 2 hr at 37° C. in a dark incubator with 5% $CO_2$. To remove extracellular dye, cells were rinsed with HBSS 3 times and then postincubated at room temperature for an additional 1 hr for complete hydrolysis of cytoplasmic fura-2 AM. The dishes with dye-loaded cells were mounted on the stage of Nikon TMS-F fluorescence inverted microscope with a Cohu 4915 CCD camera. Fluorescent images were captured alternatively at excitation wavelength of 340 and 380nM with an emission wavelength of 520 nM. After establishment of stable image baseline, the response to 1α,25-$(OH)_2$-$D_3$ and its membrane receptor (mVDR) agonist 1α,25-dihydroxylumisterol$_3$ (1α,25-$(OH)_2$-lumisterol$_3$), was determined. $[Ca^{2+}]i$ was calculated using a ratio equation as described in Grynkiewicz (Grynkiewicz, G., et al., "A new generation of $Ca^{2+}$ indicators with greatly improved fluorescent properties," *J. Biol. Chem.* (1985) pp. 3440-50, vol. 260). Each analysis evaluated responses of 8-10 representative whole cells. Images were analyzed with InCytIm2 version 4.62 imaging software (Intracellular Imaging, Cincinnati, Ohio). Images were calibrated using a fura-2 calcium imaging calibration kit (Molecular Probes, Eugene, Oreg.) to create a calibration curve in solution, and cellular calibration was accomplished using digitonin (25 μM) and pH 8.7 Tris-EGTA (100 mM) to measure maximal and minimal $[Ca^{2+}]i$ levels.

Fatty Acid Synthase (FAS) and Glycerol-3-Phosphate Dehydrogenase (GPDH) Activity Assay FAS and GPDH activity was determined spectrophotometrically in crude cytosolic extracts of human adipocytes as previously described (Shi, H., et al., "Role of the sulfonylurea receptor in regulating human adipocyte metabolism," *FASEB. J.* (1999) pp. 1833-38, vol. 13). Human adipocytes were homogenized in 250 mmol/L sucrose solution containing 1 mmol/L ethylenediamine-tetraacticacid (EDTA), 1 mmol/L dithiothreitol (DTT), and 100 μmol/L phenylmethylsulfonyl fluoride (PMSF) (pH 7.4). The homogenate was centrifuged at 18,500×g for 1 hr and the infranatant was used for measuring oxidation rate of NADPH or NADH, respectively.

Lipolysis Assay

Glycerol released into the culture medium was determined as an indicator of lipolysis, using a one-step enzymatic fluorometric method as previously described (Xue, B. Z, et al., "The agouti gene product inhibits lipolysis in human adipocytes via a $Ca^{2+}$-dependent mechanism," *FASEB. J.* (1998) pp. 1391-1396, vol. 12; Boobis, L. H., et al., "A simple one-step enzymatic fluorometric method for the determination of glycerol in 20 ul of plasma," *Clin. Chim. Acta*. (1983) pp. 173-9, vol. 132).

Northern Blot Analysis

Northern blot analysis was conducted as previously described (Shi, H., et al., "Role of the sulfonylurea receptor in regulating human adipocyte metabolism," *FASEB. J.* (1999) pp. 1833-38, vol. 13). Total RNA from human adipose tissue was extracted using $CsCl_2$ density centrifugation, run in 1% agarose gel and transferred to nylon membranes (New England Nuclear, Boston, Mass.). The membrane was hybridized with FAS cDNA probes that were radiolabeled using a random primer method. Unbound probe was removed by rinsing the membrane with 2×SSC/0.1% SDS for 30 min at room temperature and 0.1×SSC/0.1% SDS for 45 min at 55° C. Finally, the membrane was exposed to X-ray film (New England Nuclear, Boston, Mass.) at −80° C. All membranes were stripped and reprobed with β-actin as loading control. The blot image was captured using DigiPix 1260™ imager system with a CCD camera and a electronic transilluminator (ULTRA-LUM, Inc. Paramount, Calif.). ZERO-Dscan software (Scanalytics, Inc, Fairfax, Va.) was used to quantitatively analyze these images.

Statistical Analysis

All data were expressed as mean±SE. Data are evaluated for statistical significance by one way Analysis of Variance (ANOVA), and significantly different group means were then separated by the least Significant Difference (LSD) test using SPSS (SPSS Inc, Chicago, Ill.). A p value<0.05 is considered significant.

Results

To determine the direct effect of $1\alpha,25$-$(OH)_2$-$D_3$ on adipocyte $Ca^{2+}$ signaling, the $[Ca^{2+}]i$ response to $1\alpha,25$-$(OH)_2$-$D_3$ was evaluated. $1\alpha,25$-$(OH)_2$-$D_3$ induced a significant increase of $[Ca^{2+}]i$ in human adipocyte in a dose-dependent manner (p<0.05). This action was mimicked by $1\alpha,25$-dihydroxylumisterol$_3$ ($1\alpha,25$-$(OH)_2$lumisterol$_3$), a specific agonist for membrane vitamin D receptor (mVDR). $1\alpha,25$-$(OH)_2$-lumisterol$_3$ caused marked dose-responsive increases in human adipocyte $[Ca^{2+}]i$ (p<0.5), while these effects were completely prevented by pre-treatment of human adipocytes with $1\beta,25$-dihydroxyvitamin $D_3$ ($1\beta,25$-$(OH)_2$-$D_3$), a specific antagonist for mVDR.

To investigate the role of $1\alpha,25$-$(OH)_2$-$D_3$ in regulating lipid metabolism, we treated human adipocytes with $1\alpha,25$-$(OH)_2$-$D_3$ and its mVDR agonist and antagonist, using FAS and GPDH as lipogenic markers and glycerol release as a lipolytic indicator. $1\alpha,25$-$(OH)_2$-$D_3$ (5 nM) caused a 40% increase in adipocyte FAS activity over 48 hrs (p<0.05), while $1\alpha,25$-$(OH)_2$-lumisterol$_3$ exerted a more potent effect, with a 2.5 fold increase in FAS activity (p<0.001). However, pretreatment of human adipocytes with $1\beta,25$-$(OH)_2$-$D_3$ completely prevented this stimulation of FAS. A similar stimulation was observed on FAS mRNA expression, with 2 and 2.5 fold increases on $1\alpha,25$-$(OH)_2$-$D_3$ and $1\alpha,25$-$(OH)_2$-lumisterol$_3$ treatment (p<0.001), respectively, while this stimulation was completely blocked by $1\beta,25$-$(OH)_2$-$D_3$. Consistent with this, $1\alpha,25$-$(OH)_2$-$D_3$ (5 nM) stimulated a 50% increase in human adipocyte GPDH activity (p<0.05), while a markedly greater stimulation of 2.8 fold was found with $1\alpha,25$-$(OH)_2$-lumisterol$_3$ treatment (p<0.001). Although $1\beta,25$-$(OH)_2$-$D_3$ exerted little effect on $1\alpha,25$-$(OH)_2$-$D_3$ stimulated GPDH activity, it markedly inhibited $1\alpha,25$-$(OH)_2$-lumisterol$_3$ stimulated GPDH activity.

Adipocyte lipolysis responded to $1\alpha,25$-$(OH)_2$-$D_3$ and its agonist in an inverse manner to the lipogenesis. $1\alpha,25$-$(OH)_2$-$D_3$ exerted a inhibitory effect on adipocyte basal lipolysis, with a 35% reduction (p<0.05). A greater inhibition of 50% was found with $1\alpha,25$-$(OH)_2$-lumisterol$_3$ treatment (p<0.01). Conversely, this inhibition was completely prevented by pretreatment with $1\beta,25$-$(OH)_2$-$D_3$. Similarly, treatment of human adipocytes with isoproterenol resulted in a 3.2 fold increase in lipolysis (p<0.001), while $1\alpha,25$-$(OH)_2$-$D_3$ and $1\alpha,25$-$(OH)_2$-lumisterol$_3$ inhibited isoproterenol-stimulated lipolysis by 56% and 53% (p<0.001), respectively. Pretreatment with $1\alpha,25$-$(OH)_2$-$D_3$ prevented this inhibitory effect of $1\alpha,25$-$(OH)_2$-$D_3$ and $1\beta,25$-$(OH)_2$-lumisterol$_3$ on isoproterenol-stimulated lipolysis.

The data show that the calcitrophic hormone $1\alpha,25$-$(OH)_2$-$D_3$ has a role in modulating adipocyte $Ca^{2+}$ signaling, resulting in a coordinated control over lipogenesis and lipolysis. These data indicate that $1\alpha,25$-$(OH)_2$-$D_3$ plays a novel role in mediating energy homeostasis in adipose tissue and that the $1\alpha,25$-$(OH)_2$-$D_3$ mediated signaling pathways (in regulating adipocyte energy metabolism) can represent a suitable target for the development of pharmacological and/or nutritional interventions in obesity.

The data demonstrates that $1\alpha,25$-$(OH)_2$-$D_3$ elicits a non-genomic action in adipocytes, resulting in a stimulation of $[Ca^{2+}]_i$ and corresponding modulation of lipid metabolism. Although $1\alpha,25$-$(OH)_2$-$D_3$ does regulate FAS expression, this is attributed to $1\alpha,25$-$(OH)_2$-$D_3$ induced increases in $[Ca^{2+}]_i$ rather than a direct effect on FAS expression, as this effect can be mimicked by the mVDR agonist and blocked by the mVDR antagonist. Further, we have previously demonstrated modulation of $[Ca^{2+}]_i$ to correspondingly regulate FAS expression (Kim, J. H., et al., "Agouti regulation of intracellular calcium. Role of melanocortin receptor," *Am. J. Physiology*. (1997) pp. E379-E384, vol. 272; Zemel, M. B., et al., "Agouti regulation of intracellular calcium: role in the insulin resistance of viable yellow mice," *Proc. Natl. Acad. Sci. USA*. (1995) pp. 4733-4737, vol. 92; Jones, B. H., et al., "Upregulation of adipocyte metabolism by agouti protein: possible paracrine actions in yellow mouse obesity," *Am. J. Physiol*. (1996) pp. E192-E196, vol. 270; Xue, B. Z, et al., "The agouti gene product inhibits lipolysis in human adipocytes via a $Ca^{2+}$-dependent mechanism," *FASEB. J.* (1998) pp. 1391-1396, vol. 12).

The analogs of $1\alpha,25$-$(OH)_2$-$D_3$ have been extensively examined in term of their ability to generate genomic or non genomic biological response (Bouillon, B., et al., "Structure-function relationships in the vitamin D endocrine system," *Endocrine Rev*. (1995) pp. 200-57, vol. 16; Norman, A. W., "Receptor for $1\alpha,25$-$(OH)_2$-$D_3$: past, present, and future," *J. Bone. Miner. Res*. (1998) pp. 1360-69, vol. 13). Several reports (Norman, A. W., et al., "Comparison of 6-s-cis- and 6-s-trans-locked analogs of $1\alpha,25$-dihydroxyvitamin $D_3$ indicates that the 6-s-cis conformation is preferred for rapid non-genomic biological response and that neither 6-s-cis- nor 6-s-trans-locked analogs are preferred for genomic biological responses," *Mol. Endocri*. (1997) pp. 1518-31, vol. 11; Dusso, A. S., et al., "On the mechanism for the selective action of vitamin D analogs," *Endocrinology* (1991) pp. 1687-92, vol. 128.) demonstrated that 6-s-cis-locked analogs of 1α,25-(OH)$_2$-D$_3$, such as 1α,25-dihydroxylumisterol$_3$, are specific for non-genomic action, including stimulation of Ca$^{2+}$ influx, via binding to mVDR. In contrast, this analog exhibits low binding affinity to nVDR and fails to activate the genomic pathway. Further, 1,25-dihydroxyvitamin D$_3$, blocks rapid physiological response elicited by 1α,25-(OH)$_2$-D$_3$ or 1α,25-dihydroxylumisterol$_3$ but has no effects on nVDR (Norman, A., et al., "Demonstration that 1β,25-dihyroxyvitamin D$_3$ is an antagonist of the nongenomic but genomic biological response and biological profile of the three A-ring diastereomers of 1α,25-dihydroxyvitamin D$_3$", *J. Biol. Chem.* (1993) pp. 20022-30, vol. 268; Norman, A. W., et al., "1β,25-dihydroxyvitamin D$_3$ is an antagonist of 1α,25-dihydroxyvitamin D$_3$ stimulated transcaltachia (the rapid hormone stimulation of intestinal calcium transport)," *Biochem. Biophysi. Res. Com.* (1992) pp. 1450-56, vol. 189). Therefore, 1α,25-dihydroxylumisterol$_3$ is a specific agonist of non-genomic action, while 1β,25-dihydroxyvitamin D$_3$ is a specific antagonist of non-genomic action. It is noteworthy that 1α,25-dihydroxylumisterol$_3$ exerted more potent effects in modulating adipocyte [Ca$^{2+}$]$_i$ and corresponding lipid metabolism, and that 1β,25-dihydroxyvitamin D$_3$ completely blocked these effects. This suggests that 1α,25-dihydroxylumisterol$_3$ acts on the mVDR solely to generate non-genomic action in adipocytes, whereas 1α,25-(OH)$_2$-D$_3$ may target both mVDR and nVDR to mediate non-genomic and genomic actions which may interact with each other in signal response and affect the modulation of lipid metabolism. These data further demonstrate that 1α,25-(OH)$_2$-D$_3$ mediated non-genomic action via mVDR may play a major role in regulating adipocyte lipogenesis and lipolysis.

Regulation of adipocyte metabolism via 1α,25-(OH)$_2$-D$_3$ signaling pathways may play an important role in the development of obesity in vivo. Several lines of evidence demonstrate that circulating 1α,25-(OH)$_2$-D$_3$ level is elevated in obese humans (Andersen, T., et al., "Secondary hyperparathyroidism of morbid obesity regresses during weight reduction," *Metabolism* (1988) pp. 425-8, vol. 37; Bell, N. H., et al., "Evidence for alteration of the vitamin D-endocrine system in obese subjects," *J. Clin. Invest.* (1985) pp. 370-3, vol. 76; Bell, N. H., et al., "Evidence of a probable role for 25-hydroxyvitamin D in the regulation of human calcium metabolism," *J. Bone. Miner. Res.* (1988) pp. 489-95, vol. 3; Epstein, S., et al., "Evidence that obesity dose not influence the vitamin D-endocrine system in blacks," *J. Bone. Miner. Res.* (1986) pp. 181-4, vol. 1). Accordingly, 1α,25-(OH)$_2$-D$_3$ mediated signaling pathway in regulating adipocyte energy homeostasis may represent a suitable target for the development of pharmacological and/or nutritional interventions in obesity. Previous studies showed that increasing dietary calcium suppressed 1α,25-(OH)$_2$-D$_3$ levels (Resnick, L., "The cellular ionic basis of hypertension and allied clinic conditions," *Prog. Cardiovasc. Dis.* (1999) pp. 1-22, vol. 42; Sanchez, M., et al., "Oral calcium supplementation reduces intraplateletfree calcium concentration and insulin resistance in essential hypertensive patients," *Hypertension* (1997) pp. 531-6, vol. 29). Accordingly, we tested the hypothesis that dietary calcium suppression of 1α,25-(OH)$_2$-D$_3$ would reduce adipocyte [Ca$^{2+}$]$_i$ and thereby inhibit triglyceride accumulation by coordinated control over lipogenesis and lipolysis. Our data demonstrated that suppression of 1α,25-(OH)$_2$-D$_3$ by increasing dietary calcium decreased adipocyte intracellular Ca$^{2+}$, stimulated lipolysis, inhibited lipogenesis, increased adipocyte uncoupling protein 2 (UCP2) expression and core temperature in aP2-agouti transgenic mice and that dietary calcium not only attenuated diet-induced obesity but also accelerated weight loss and fat mass reduction secondary to caloric restriction (Zemel, M. B., et al., "Regulation of adiposity by dietary calcium," *FASEB. J.* (2000) pp. 1132-38, vol. 14; Shi, H., et al., "Effects of dietary calcium on adipocyte lipid metabolism and body weight regulation in energy-restricted aP2-agouti transgenic mice," *FASEB. J.* express article 10.1096/fj.00-0584fje. Published online Dec. 8, 2000).

the data suggest that 1α,25-(OH)$_2$-D$_3$ modulates adipocyte Ca$^{2+}$ signaling and, consequently, exerts a coordinated control over lipogenesis and lipolysis. Thus, a direct inhibition of 1α,25-(OH)$_2$-D$_3$ induced [Ca$^{2+}$]i can contribute to an anti-obesity effect by dietary calcium, and the mVDR mediated non-genomic pathway is an important target for development of therapeutic interventions in obesity.

It should be understood that the examples and embodiments described herein are for illustrative purposes only and that various modifications or changes in light thereof will be suggested to persons skilled in the art and are to be included within the spirit and purview of this application and the appended claims.

We claim:

1. A method of regulating body weight comprising administering to an individual in need thereof an antagonist of calcitrophic hormone (1,25-(OH)$_2$-D) activity, wherein the antagonist is 1-β,25-dihydroxyvitamin D, in an amount effective to block calcitrophic hormone (1,25-(OH)$_2$-D) activity in adipocytes of said individual, and increase intracellular calcium, said antagonist inducing weight loss, and/or increasing metabolic consumption of adipose tissue.

2. The method of claim 1, wherein the individual has Grade I obesity.

3. The method of claim 1, wherein the individual has Grade II obesity.

4. The method of claim 1, wherein the individual has Grade III obesity.

5. The method of claim 1, wherein the antagonist is contained in a liquid.

6. The method of claim 1, wherein the calcitrophic hormone activity in adipocytes that is blocked is selected from one or more of inhibiting lipolysis, stimulating lipogenesis, increasing adiposity, stimulating triglyceride accumulation, increasing intracellular calcium concentration ([Ca$^{2+}$]$_i$), inhibiting adipocyte uncoupling protein 2 (UCP2) expression and/or stimulating fatty acid synthase (FAS) activity.

7. The method of claim 1, wherein the antagonist reduces the risk of an obesity related health problem selected from the group consisting of coronary artery disease, stroke, diabetes, osteoarthritis, ligament injuries, perineal dermatitis, diabetes mellitus, cardiomyopathy, and urologic syndrome.

8. The method of claim 1, wherein the individual is a human.

9. The method of claim 1, wherein the individual is a non-human animal.

10. The method of claim 1, wherein the antagonist brings about an effect selected from the group consisting of suppressing adiposity, inhibiting triglyceride accumulation, reducing intracellular calcium concentration ([Ca$^{2+}$]$_i$, increasing adipocyte uncoupling protein 2 (UCP2) expression, increasing core temperature, accelerating weight loss and fat mass reduction in an individual under caloric restriction, and combinations thereof.

11. The method of claim 1, wherein the antagonist suppresses or decreases intracellular calcium concentration ([Ca$^{2+}$]$_i$).

12. The method of claim 1, wherein the antagonist blocks the action of 1,25-(OH)2-D in adipocytes.

13. The method of claim 1, wherein the administering decreases the levels of calcitrophic hormones in the adipocytes.

14. The method of claim 1, wherein the antagonist stimulates lipolysis and inhibits lipogenesis.

15. The method of claim 1, wherein the antagonist blocks calcitrophic hormone induced inhibition of lipolysis in adipocytes.

16. The method of claim 1, wherein the antagonist suppresses adiposity and inhibits triglyceride accumulation by stimulating lipolysis and inhibiting lipogenesis.

17. The method of claim 1, wherein the antagonist increases core temperature.

18. The method of claim 1, wherein the antagonist induces a metabolic state in which the energy metabolism is shifted from energy storage to energy expenditure.

19. The method of claim 1, wherein the antagonist accelerates weight loss and/or fat mass reduction in an individual under caloric restriction.

\* \* \* \* \*